(12) United States Patent
Singer

(10) Patent No.: US 9,663,830 B2
(45) Date of Patent: May 30, 2017

(54) METHODS AND COMPOSITIONS FOR THE DIAGNOSIS OF SEPSIS USING GAMMA PEPTIDE NUCLEIC ACIDS

(71) Applicant: HELIXBIND, Marlborough, MA (US)

(72) Inventor: Alon Singer, Brighton, MA (US)

(73) Assignee: HELIXBIND, Marlborough, MA (US)

( * ) Notice: Subject to any disclaimer, the term of this patent is extended or adjusted under 35 U.S.C. 154(b) by 365 days.

(21) Appl. No.: 14/402,028

(22) PCT Filed: May 17, 2013

(86) PCT No.: PCT/US2013/041628
§ 371 (c)(1),
(2) Date: Nov. 18, 2014

(87) PCT Pub. No.: WO2013/176992
PCT Pub. Date: Nov. 28, 2013

(65) Prior Publication Data
US 2015/0099657 A1    Apr. 9, 2015

Related U.S. Application Data

(60) Provisional application No. 61/649,342, filed on May 20, 2012, provisional application No. 61/799,772, filed on Mar. 15, 2013.

(51) Int. Cl.
    C12Q 1/68      (2006.01)
(52) U.S. Cl.
    CPC .......... *C12Q 1/689* (2013.01); *C12Q 1/6816* (2013.01); *C12Q 1/6883* (2013.01); *C12Q 1/6895* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 7,960,360 B2 | 6/2011 | Grandis et al. |
| 2003/0082535 A1 | 5/2003 | Leushner et al. |
| 2007/0031850 A1 | 2/2007 | Mounts et al. |
| 2009/0208933 A1 | 8/2009 | Pachot et al. |
| 2009/0286249 A1 | 11/2009 | Becker et al. |

FOREIGN PATENT DOCUMENTS

| WO | WO-2012/138955 | 10/2012 |
| WO | WO-2013/074601 | 5/2013 |

OTHER PUBLICATIONS

International Search Report for PCT/US2013/041628 mailed Dec. 13, 2013.
Kuhn, et al., "Sequence specificity at targeting double-stranded DNA with a γ-PNA oligomer modified with guanidinium G-clamp nucleobases," Artificial DNA: PNA & XNA 1:1, 45-53; Jul./Aug./Sep. 2010.

*Primary Examiner* — Christopher M Gross
(74) *Attorney, Agent, or Firm* — James F. Ewing; Foley & Lardner LLP

(57) ABSTRACT

The present disclosure provides for composition of γPNA probes. Additionally, the present disclosure provide for methods and kits using γPNA probes for the prognosis of sepsis. In some embodiments, wherein the γPNA capture probes and γPNA reporter probes comprise one or more functional moiety selected from the group consisting of: a binding molecule, a spacer group, a linker group, a hydrophobicity-changing group, a charge-inducing group, and a structural charge-inducing group.

39 Claims, 4 Drawing Sheets

SEQUENCE LISTING

```
<160> NUMBER OF SEQ ID NOS: 315

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
cggaacatct tcttc                                                        15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
tcagaagatg cggaa                                                        15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 3
cctgataagc gtgag                                                    15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
gagtccactt aggcc                                                    15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cacttaggcc cacca                                                    15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
aggcccacca ttatt                                                    15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
aacggacgag aagct                                                    15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tcctttgaca actct                                                    15

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
aacggacgag aagct                                                            15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
agagatagag ccttc                                                            15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tttgacaact ctaga                                                            15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
cttctctgat gttag                                                            15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
ggataatatt ttgaa                                                            15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
ttcaaaagtg aaaga                                                            15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
agacggtctt gctgt                                              15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
atccgcgctg catta                                              15

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
agaacatatg tgtaa                                              15

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
taacctttta ggagc                                              15

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
acaaggacgt tagta                                              15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
ctttcctccc gagtg                                              15

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
cctacccatc agagg                                              15

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
ggacgttagt aactg                                                    15

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
cttgctccac cggaa                                                    15

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24 cttttccac cggag                                                     15

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
atggttttga tttga                                                    15

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26 cttttccac cggag                                                     15

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
cgtataacaa tcgaa                                                    15

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
cgtataacaa tcaaa                                                     15

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
aacaggaaga agctt                                                     15

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
ggagtaaagt taata                                                     15

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
atacctttgc tcatt                                                     15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
catctgatac tggca                                                     15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
ttgcttcttt gctga                                                     15

-continued

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
agcttgagtc tcgta                                                        15

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
gctcctctga cgtta                                                        15

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
ataatatatt gaacc                                                        15

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
ttcaatagtg aaaga                                                        15

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
aactatgcac gtctt                                                        15

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
gagcggatga aggga                                                        15

<210> SEQ ID NO 40

```
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
cttgctcctg gattc                                                    15

<210> SEQ ID NO 41
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
aatctgcctg gtagt                                                    15

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
ataacgtccg gaaac                                                    15

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
ccgcatacgt cctga                                                    15

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
agatgagcct aggtc                                                    15

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
gacgatccgt aactg                                                    15

<210> SEQ ID NO 46
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
cagtaagtta atacc                                                    15

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
caacagaata agcac                                                    15

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
tccaaaacta ctgag                                                    15

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
ctgagctaga gtacg                                                    15

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
aatttcctgt gtagc                                                    15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
gcgtagatat aggaa                                                    15

<210> SEQ ID NO 52
<211> LENGTH: 15
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 52
accacctgga ctgat                                                     15

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
tgtcgactag ccgtt                                                     15

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
agccgttggg atcct                                                     15

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
tgagatctta gtggc                                                     15

<210> SEQ ID NO 56
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
aactcagaca caggt                                                     15

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
ttgtccttag ttacc                                                     15

<210> SEQ ID NO 58
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 58
ctgaaggagg agctt                                                          15

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
aggagcttgc ttctc                                                          15

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
atgacatttg cttaa                                                          15

<210> SEQ ID NO 61
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
acttgcatca ctacc                                                          15

<210> SEQ ID NO 62
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
aatggacgga agtct                                                          15

<210> SEQ ID NO 63
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
aagaacgagt gtgag                                                          15

<210> SEQ ID NO 64
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 64
aaagttcaca ctgtg                                                       15

<210> SEQ ID NO 65
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
tatcttacca gaaag                                                       15

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
ttagataagt ctgaa                                                       15

<210> SEQ ID NO 67
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
aaaggctgtg gctta                                                       15

<210> SEQ ID NO 68
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
ttaaccatag taggc                                                       15

<210> SEQ ID NO 69
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
aaactgttta acttg                                                       15

<210> SEQ ID NO 70
<211> LENGTH: 15
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 70
acttgagtgc aagag                                                         15

<210> SEQ ID NO 71
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
tctctggctt gtaac                                                         15

<210> SEQ ID NO 72
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
cctctgaccg ctcta                                                         15

<210> SEQ ID NO 73
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
agaactggtg cttgc                                                         15

<210> SEQ ID NO 74
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
ctggtgcttg caccg                                                         15

<210> SEQ ID NO 75
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
ttgcaccggt tcaag                                                         15

<210> SEQ ID NO 76
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 76
taacctacct catag                                               15

<210> SEQ ID NO 77
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
ataagagaga ctaac                                               15

<210> SEQ ID NO 78
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
agactaacgc atgtt                                               15

<210> SEQ ID NO 79
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
agtaatttaa aaggg                                               15

<210> SEQ ID NO 80
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
aattgctcca ctatg                                               15

<210> SEQ ID NO 81
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
ctccactatg agatg                                               15

<210> SEQ ID NO 82
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 82
ttagagaaga atgat                                                    15

<210> SEQ ID NO 83
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
gaaaatccac caagt                                                    15

<210> SEQ ID NO 84
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
tgacggtaac taacc                                                    15

<210> SEQ ID NO 85
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
aaaggcattg gctca                                                    15

<210> SEQ ID NO 86
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
ctcaaccaat gtacg                                                    15

<210> SEQ ID NO 87
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
aaactggaga acttg                                                    15

<210> SEQ ID NO 88
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
```
cttgagtgca gaagg                                                        15

<210> SEQ ID NO 89
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
gcttagtgcc ggagc                                                        15

<210> SEQ ID NO 90
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
atagagtttt acttc                                                        15

<210> SEQ ID NO 91
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
ggtacatcgg tgaca                                                        15

<210> SEQ ID NO 92
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
aaggcgataa ggtta                                                        15

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
tgccagcggt taggc                                                        15

<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
aaggcgatga ggtta                                                          15

<210> SEQ ID NO 95
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
aaggcgttaa ggtta                                                          15

<210> SEQ ID NO 96
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
ataaccttgg cgatt                                                          15

<210> SEQ ID NO 97
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
tgccagcggt ccggc                                                          15

<210> SEQ ID NO 98
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
aacaggagaa agctt                                                          15

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
tttcttgctg acgag                                                          15

<210> SEQ ID NO 100
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
ggatctgccc gatag                                                          15

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
ataatgtcta cggac                                                         15

<210> SEQ ID NO 102
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
tacggaccaa agcag                                                         15

<210> SEQ ID NO 103
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
ttgcactatc ggatg                                                         15

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
cggatgaacc catat                                                         15

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
aatacccttg tcaat                                                         15

<210> SEQ ID NO 106
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
tcaattaagt cagat                                                         15

```
<210> SEQ ID NO 107
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
atctgaaact ggttg                                                       15

<210> SEQ ID NO 108
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
atttagaggt tgtgg                                                       15

<210> SEQ ID NO 109
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
ttgtggtctt gaacc                                                       15

<210> SEQ ID NO 110
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
agcgaatcct ttaga                                                       15

<210> SEQ ID NO 111
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
gactgggaca acttc                                                       15

<210> SEQ ID NO 112
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
ataatatgtt gaacc                                                       15
```

```
<210> SEQ ID NO 113
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
gtcttaggat cgtaa                                                    15

<210> SEQ ID NO 114
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
ggataacata ttgaa                                                    15

<210> SEQ ID NO 115
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
aaaggcggct ttgct                                                    15

<210> SEQ ID NO 116
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
tctgttatca gggaa                                                    15

<210> SEQ ID NO 117
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
gtacctgatc agaaa                                                    15

<210> SEQ ID NO 118
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
agatggcttt gctat                                                    15

<210> SEQ ID NO 119
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
gagatagaag tttcc                                                     15

<210> SEQ ID NO 120
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
aaggtggtga gctta                                                     15

<210> SEQ ID NO 121
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 121
ttaatacgtt catca                                                     15

<210> SEQ ID NO 122
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 122
aaggtagctt gctac                                                     15

<210> SEQ ID NO 123
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 123
ttgctaccgg accta                                                     15

<210> SEQ ID NO 124
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 124
aatgcttagg aatct                                                     15

<210> SEQ ID NO 125
<211> LENGTH: 15
```

-continued

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 125
aatctgccta ttagt                                                          15

<210> SEQ ID NO 126
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126
acaacatctc gaaag                                                          15

<210> SEQ ID NO 127
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 127
aaagggatgc taata                                                          15

<210> SEQ ID NO 128
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 128
accttgcgct aatag                                                          15

<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 129
atgagcctaa gtcgg                                                          15

<210> SEQ ID NO 130
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 130
cgatctgtag cgggt                                                          15

<210> SEQ ID NO 131
<211> LENGTH: 15
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 131
aaccctgatc cagcc                                                    15

<210> SEQ ID NO 132
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 132
aggctacttt agtta                                                    15

<210> SEQ ID NO 133
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 133
tttagttaat accta                                                    15

<210> SEQ ID NO 134
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 134
tacctagaga tagtg                                                    15

<210> SEQ ID NO 135
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 135
atagtggacg ttact                                                    15

<210> SEQ ID NO 136
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 136
cagccatctg gccta                                                    15

<210> SEQ ID NO 137
<211> LENGTH: 15
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 137
gcctaatact gacgc                                                      15

<210> SEQ ID NO 138
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 138
tctactagcc gttgg                                                      15

<210> SEQ ID NO 139
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 139
cctttgaggc tttag                                                      15

<210> SEQ ID NO 140
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140
cgataagtag accgc                                                      15

<210> SEQ ID NO 141
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 141
gtcgcaagac taaaa                                                      15

<210> SEQ ID NO 142
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 142
tggccttgac atact                                                      15

<210> SEQ ID NO 143
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 143
atactagaaa ctttc                                                      15

<210> SEQ ID NO 144
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
aatctagata caggt                                                      15

<210> SEQ ID NO 145
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 145
ttttccttac ttgcc                                                      15

<210> SEQ ID NO 146
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 146
ccagcatttc ggatg                                                      15

<210> SEQ ID NO 147
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
actttaagga tactg                                                      15

<210> SEQ ID NO 148
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148
ttgctacaca gcgat                                                      15

<210> SEQ ID NO 149
<211> LENGTH: 15
<212> TYPE: DNA
<213> ORGANISM: Artificial Sequence
<220> FEATURE:
<223> OTHER INFORMATION: Description of Artificial Sequence: Synthetic
```

```
            probe

<400> SEQUENCE: 149
atgtgatgct aatct                                                    15

<210> SEQ ID NO 150
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
taatctcaaa aagcc                                                    15

<210> SEQ ID NO 151
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 151
aagccgatcg tagtc                                                    15

<210> SEQ ID NO 152
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
aatgccgcgg tgaat                                                    15

<210> SEQ ID NO 153
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153
tagcctaact gcaaa                                                    15

<210> SEQ ID NO 154
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 154
aacggcagca cagta                                                    15

<210> SEQ ID NO 155
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 155
taagagcttg ctctt                                                      15

<210> SEQ ID NO 156
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
gaatacatcg gaatc                                                      15

<210> SEQ ID NO 157
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 157
aaacttacgc taata                                                      15

<210> SEQ ID NO 158
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 158
atccagctgg ttaat                                                      15

<210> SEQ ID NO 159
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159
gtacccaaag aataa                                                      15

<210> SEQ ID NO 160
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 160
ttgtttaagt ctgtt                                                      15

<210> SEQ ID NO 161
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 161
agctacctgg accaa                                                    15

<210> SEQ ID NO 162
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 162
tgcaatttgg cacgc                                                    15

<210> SEQ ID NO 163
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 163
aacgcgttaa gttcg                                                    15

<210> SEQ ID NO 164
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 164
ctgcaagccg gcgac                                                    15

<210> SEQ ID NO 165
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 165
agaaacccta tctca                                                    15

<210> SEQ ID NO 166
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 166
agcattgctg cggtg                                                    15

<210> SEQ ID NO 167
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 167
aacagataag gagct                                                     15

<210> SEQ ID NO 168
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
aacagacgag gagct                                                     15

<210> SEQ ID NO 169
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 169
aacagacaag gagct                                                     15

<210> SEQ ID NO 170
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 170
ctcctttgac gttag                                                     15

<210> SEQ ID NO 171
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
ctcctctgac gttag                                                     15

<210> SEQ ID NO 172
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172
ctcttttgac gttag                                                     15

<210> SEQ ID NO 173
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173
cttctctgac gttag                                                15

<210> SEQ ID NO 174
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
ggataatatt tcgaa                                                15

<210> SEQ ID NO 175
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 175
ggataacata ttgaa                                                15

<210> SEQ ID NO 176
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
ggataatata ttgaa                                                15

<210> SEQ ID NO 177
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
ggataatatg ttgaa                                                15

<210> SEQ ID NO 178
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
agatggtttt gctat                                                15

<210> SEQ ID NO 179
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 179
aggcggcttt gctgt                                                15

```
<210> SEQ ID NO 180
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 180
agacggtttt gctgt                                                    15

<210> SEQ ID NO 181
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 181
agatggcttt gctat                                                    15

<210> SEQ ID NO 182
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 182
acccgcgccg tatta                                                    15

<210> SEQ ID NO 183
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 183
acctgcgccg tatta                                                    15

<210> SEQ ID NO 184
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 184
atccgcgccg tatta                                                    15

<210> SEQ ID NO 185
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 185
atccgcgccg catta                                                    15
```

```
<210> SEQ ID NO 186
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
agaacatacg tgtaa                                                    15

<210> SEQ ID NO 187
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 187
agaacaaacg tgtaa                                                    15

<210> SEQ ID NO 188
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 188
agaacaaatg tgtaa                                                    15

<210> SEQ ID NO 189
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
taaccatttg gagct                                                    15

<210> SEQ ID NO 190
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 190
taaccattta tggag                                                    15

<210> SEQ ID NO 191
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 191
aatgtcttcg gactc                                                    15
```

```
<210> SEQ ID NO 192
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
catctttctg atgcg                                                      15

<210> SEQ ID NO 193
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 193
ggctagcctt ttggc                                                      15

<210> SEQ ID NO 194
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 194
atcttttttg atgcg                                                      15

<210> SEQ ID NO 195
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
tggctagcct ttttg                                                      15

<210> SEQ ID NO 196
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 196
tattcagtag tcaga                                                      15

<210> SEQ ID NO 197
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 197
ctttactaca tggta                                                      15

<210> SEQ ID NO 198
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 198
atggtataac tgtgg                                                       15

<210> SEQ ID NO 199
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 199
atgcttaaaa tctcg                                                       15

<210> SEQ ID NO 200
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 200
tccgattttt tcgtg                                                       15

<210> SEQ ID NO 201
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 201
tgtactggaa tgcac                                                       15

<210> SEQ ID NO 202
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 202
aaccccaagt ccttg                                                       15

<210> SEQ ID NO 203
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 203
ttgtggcttg gcggc                                                       15

<210> SEQ ID NO 204
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 204
acgtttggtt ctatt                                                          15

<210> SEQ ID NO 205
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 205
tattcaattg tcaga                                                          15

<210> SEQ ID NO 206
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 206 tgtttttta gtgac                                                           15

<210> SEQ ID NO 207
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 207
taaatagtgg tgcta                                                          15

<210> SEQ ID NO 208
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 208
atttgctggt tgtcc                                                          15

<210> SEQ ID NO 209
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 209
tatcggtttc aagcc                                                          15

<210> SEQ ID NO 210
<211> LENGTH: 15
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 210
agcgagtcta acctt                                                     15

<210> SEQ ID NO 211
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 211
tcttggtaat cttgt                                                     15

<210> SEQ ID NO 212
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 212
ttctgggtag ccatt                                                     15

<210> SEQ ID NO 213
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 213
gccatttatg gcgaa                                                     15

<210> SEQ ID NO 214
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 214
ggtagccatt tatgg                                                     15

<210> SEQ ID NO 215
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 215
ctatcgactt caagt                                                     15

<210> SEQ ID NO 216
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 216
taccttacta catgg                                                      15

<210> SEQ ID NO 217
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 217
actacatgga tacct                                                      15

<210> SEQ ID NO 218
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 218
tgctaaaaac ctcga                                                      15

<210> SEQ ID NO 219
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 219
taaaaaacca atgcc                                                      15

<210> SEQ ID NO 220
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 220
taacgaatcg catgg                                                      15

<210> SEQ ID NO 221
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 221
taccatggtg gcaac                                                      15

<210> SEQ ID NO 222
<211> LENGTH: 15
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 222
aatctaaatc cctta                                                      15

<210> SEQ ID NO 223
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 223
agtactggtc cggct                                                      15

<210> SEQ ID NO 224
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 224
gaacctcatg gcctt                                                      15

<210> SEQ ID NO 225
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 225
gccttcactg gctgt                                                      15

<210> SEQ ID NO 226
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 226
tttctatgat gaccc                                                      15

<210> SEQ ID NO 227
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 227
tcggccctta aatag                                                      15

<210> SEQ ID NO 228
<211> LENGTH: 15
<212> TYPE: DNA
<213> ORGANISM: Artificial Sequence
<220> FEATURE:
<223> OTHER INFORMATION: Description of Artificial Sequence: Synthetic probe

<400> SEQUENCE: 228
gagtacatca ccttg                                                    15

<210> SEQ ID NO 229
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 229
cttgttaaac cctgt                                                    15

<210> SEQ ID NO 230
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 230
agctcgtgcc gatta                                                    15

<210> SEQ ID NO 231
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 231
ggactaccag ggtat                                                    15

<210> SEQ ID NO 232
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 232
accagggtat ctaat                                                    15

<210> SEQ ID NO 233
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 233
cgggaacgta ttcac                                                    15

<210> SEQ ID NO 234
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 234
cagcagccgc ggtaa                                                             15

<210> SEQ ID NO 235
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 235
atgtggttta attcg                                                             15

<210> SEQ ID NO 236
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 236
gtgccagcag ccgc                                                              14

<210> SEQ ID NO 237
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 237
aacgagcgca accc                                                              14

<210> SEQ ID NO 238
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 238
gtggtttaat tcga                                                              14

<210> SEQ ID NO 239
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 239
accttgttac gactt                                                             15

<210> SEQ ID NO 240
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 240
cgacagagtt tgatc 15

<210> SEQ ID NO 241
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 241
accttgttac gactt 15

<210> SEQ ID NO 242
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 242
cagccgcggt aatac 15

<210> SEQ ID NO 243
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 243
aacaggatta gatac 15

<210> SEQ ID NO 244
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 244
gtcgtcagct cgtgt 15

<210> SEQ ID NO 245
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 245
atgttgggtt aagtc 15

<210> SEQ ID NO 246
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 246

```
gaatcgctag taatc                                                    15

<210> SEQ ID NO 247
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 247
cttgtacaca ccgcc                                                    15

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 248
ggactaccag ggtatctaat                                               20

<210> SEQ ID NO 249
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 249
gtgaaactgc gaatg                                                    15

<210> SEQ ID NO 250
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 250
ctgcgaatgg ctcat                                                    15

<210> SEQ ID NO 251
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 251
gctcattaaa tcagt                                                    15

<210> SEQ ID NO 252
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 252
```
tcagttatcg tttat					15

<210> SEQ ID NO 253
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 253
cgtttatttg atagt					15

<210> SEQ ID NO 254
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 254
tctagagcta ataca					15

<210> SEQ ID NO 255
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 255
tagagctaat acatg					15

<210> SEQ ID NO 256
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 256
tgtatttatt agata					15

<210> SEQ ID NO 257
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 257
ttattagata aaaaa					15

<210> SEQ ID NO 258
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 258
tggttcattc aaatt					15

<210> SEQ ID NO 259
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 259
ttcaaatttc tgccc                                                    15

<210> SEQ ID NO 260
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 260
ctgccctatc aactt                                                    15

<210> SEQ ID NO 261
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 261
aactttcgat ggtag                                                    15

<210> SEQ ID NO 262
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 262
tcgatggtag gatag                                                    15

<210> SEQ ID NO 263
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 263
agggttcgat tccgg                                                    15

<210> SEQ ID NO 264
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 264
agcctgagaa acggc                                                    15

<210> SEQ ID NO 265
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 265
agaaacggct accac                                                       15

<210> SEQ ID NO 266
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 266
ctaccacatc caagg                                                       15

<210> SEQ ID NO 267
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 267
atccaaggaa ggcag                                                       15

<210> SEQ ID NO 268
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 268
aaggcagcag gcgcg                                                       15

<210> SEQ ID NO 269
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 269
aggcgcgcaa attac                                                       15

<210> SEQ ID NO 270
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 270
caaattaccc aatcc                                                       15

-continued

```
<210> SEQ ID NO 271
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 271
gaggtagtga caata                                                    15

<210> SEQ ID NO 272
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 272
gtaattggaa tgagt                                                    15

<210> SEQ ID NO 273
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 273
tggaatgagt acaat                                                    15

<210> SEQ ID NO 274
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 274
ccttaacgag gaaca                                                    15

<210> SEQ ID NO 275
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 275
caagtctggt gccag                                                    15

<210> SEQ ID NO 276
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 276
taattccagc tccaa                                                    15

<210> SEQ ID NO 277
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 277
agcgtatatt aaagt                                                        15

<210> SEQ ID NO 278
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 278
ttaaagttgt tgcag                                                        15

<210> SEQ ID NO 279
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 279
gttgcagtta aaaag                                                        15

<210> SEQ ID NO 280
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 280
agctcgtagt tgaac                                                        15

<210> SEQ ID NO 281
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 281
aaattagagt gttca                                                        15

<210> SEQ ID NO 282
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 282
gtgttcaaag caggc                                                        15

<210> SEQ ID NO 283
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 283
attagcatgg aataat                                                    16

<210> SEQ ID NO 284
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 284
ggttctattt tgttg                                                     15

<210> SEQ ID NO 285
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 285
tgttggtttc tagga                                                     15

<210> SEQ ID NO 286
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 286
gtcagaggtg aaatt                                                     15

<210> SEQ ID NO 287
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 287
tgaaattctt ggatt                                                     15

<210> SEQ ID NO 288
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 288
tgaagactaa ctact                                                     15

<210> SEQ ID NO 289
<211> LENGTH: 15
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 289
tactgcgaaa gcatt                                                        15

<210> SEQ ID NO 290
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 290
gttttcatta atca                                                         14

<210> SEQ ID NO 291
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 291
aacgaaagtt aggg                                                         14

<210> SEQ ID NO 292
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 292
gatcagatac cgtcg                                                        15

<210> SEQ ID NO 293
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 293
accgtcgtag tctta                                                        15

<210> SEQ ID NO 294
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 294
tagtcttaac cataa                                                        15

<210> SEQ ID NO 295
<211> LENGTH: 15
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 295
accataaact atgcc                                                         15

<210> SEQ ID NO 296
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 296
tatgccgact agggat                                                        16

<210> SEQ ID NO 297
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 297
tcggcacctt acgag                                                         15

<210> SEQ ID NO 298
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 298
tacgagaaat caaag                                                         15

<210> SEQ ID NO 299
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 299
agtatggtcg caagg                                                         15

<210> SEQ ID NO 300
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 300
ggctgaaact taaag                                                         15

<210> SEQ ID NO 301
<211> LENGTH: 15
<212> TYPE: DNA
<213> ORGANISM: Artificial Sequence
<220> FEATURE:

```
<223> OTHER INFORMATION: Description of Artificial Sequence: Synthetic
      probe

<400> SEQUENCE: 301
agcctgcggc ttaat                                                    15

<210> SEQ ID NO 302
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 302
ttaatttgac tcaac                                                    15

<210> SEQ ID NO 303
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 303
aaactcacca ggtcca                                                   16

<210> SEQ ID NO 304
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 304
tggagtgatt tgtct                                                    15

<210> SEQ ID NO 305
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 305
tgtctgctta attgcgat                                                 18

<210> SEQ ID NO 306
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 306
aacaggtctg tgatg                                                    15

<210> SEQ ID NO 307
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 307
tgtgatgccc ttaga                                                     15

<210> SEQ ID NO 308
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 308
gcgcgctaca ctgac                                                     15

<210> SEQ ID NO 309
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 309
ttgctcttca acgag                                                     15

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
agagtttgat cctggctcag                                                20

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
atcggctacc ttgttacgac ttc                                            23

<210> SEQ ID NO 312
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
aaatcagtta tcgtttattt gatagt                                         26

<210> SEQ ID NO 313
<211> LENGTH: 19
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 313
attcctcgtt gaagagcaa                                                    19

<210> SEQ ID NO 314
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 314
gcgaacggac gagaagcttg ct                                                22

<210> SEQ ID NO 315
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 315
gcgaacagac gaggagcttg ct                                                22
```

METHODS AND COMPOSITIONS FOR THE DIAGNOSIS OF SEPSIS USING GAMMA PEPTIDE NUCLEIC ACIDS

This application is the U.S. National Stage of International Application No. PCT/US2013/041628, with international filing date May 17, 2013, which claims the benefit of and priority to U.S. Provisional Application No. 61/649,342, filed May 20, 2012 and U.S. Provisional Application No. 61/799,772, filed on Mar. 15, 2013, the contents of which are incorporated herein by reference in their entireties.

FIELD OF THE DISCLOSURE

This disclosure generally relates to methods, compositions, and kits that use peptide nucleic acid (PNA) as probes for the diagnosis of sepsis.

BACKGROUND

Sepsis, a spectrum of severe immune disorders triggered by systemic infections, is a leading cause of morbidity and mortality. In the U.S. alone, 751,000 sepsis cases occur annually, leading to 210,000 mortalities and an economic burden of $24 B. The primary causes of sepsis are usually symptomatic bacteremia or fungemia, a diagnosis that can only be determined by laboratory testing. Detection of the infecting pathogen is essential to identifying patients and initiating the proper antimicrobial therapy to avert or lessen a sepsis reaction. Traditionally, the first step in this process is a time-intensive step of culturing the unknown pathogen from a patient specimen for a period of 1-5 days. The culturing step results in a delay of effective treatment just at the earliest time of infection, which is a crucial therapeutic window when therapy has the maximum benefit. Each single hour delay in proper treatment increases the probability of mortality by 7.6%.

SUMMARY

The present disclosure describes methods for diagnosing sepsis that do not require the time-consuming culturing step. In one embodiment, the method comprises first contacting a plurality of γPNA capture probes to genomic material in a clinical sample obtained from a subject suspected of having sepsis, wherein the γPNA capture probes comprise at least one sequence from one or more of the groups of probes selected from the group consisting of: SEQ ID NOS: 1-18 (provided in Table 1), SEQ ID NOS: 19-22 (provided in Table 2), SEQ ID NOS: 23-28 (provided in Table 3), SEQ ID NOS: 29-34 (provided in Table 4), SEQ ID NOS: 35-38 (provided in Table 5), SEQ ID NOS: 39-57 (provided in Table 6), SEQ ID NOS: 58-72 (provided in Table 7), SEQ ID NOS: 73-91 (provided in Table 8), SEQ ID NOS: 92-94 (provided in Table 9), SEQ ID NOS: 95-97 (provided in Table 10), SEQ ID NOS: 98-110 (provided in Table 11), SEQ ID NOS: 111-113 (provided in Table 12), SEQ ID NOS: 114-117 (provided in Table 13), SEQ ID NOS: 118-119 (provided in Table 14), SEQ ID NOS: 120-121 (provided in Table 15), SEQ ID NOS: 122-153 (provided in Table 16), SEQ ID NOS: 154-166 (provided in Table 17), SEQ ID NOS: 167-190 (provided in Table 18), SEQ ID NOS: 191-193 (provided in Table 19), SEQ ID NOS: 194-196 (provided in Table 20), SEQ ID NOS: 197-211 (provided in Table 21), SEQ ID NOS: 212-215 (provided in Table 22), SEQ ID NOS: 216-230 (provided in Table 23), complementary sequence thereof, and functional equivalents thereof; followed by the steps of heating the γPNA capture probes and the sample; invading a plurality of targeted sepsis-related genomic material by the γPNA capture probes; and detecting a presence of one or more targeted genomic material. Detection of the presence of targeted genomic material indicates the presence of a sepsis infection.

In some embodiments, the detection of targeted genomic material comprises of adding a plurality of γPNA reporter probes, which comprise of at least one sequence from one or both of the groups of probes: SEQ ID NOS: 231-248 (provided in Table 24) and SEQ ID NOS: 249-309 (provided in Table 25), complementary sequence thereof, and functional equivalents thereof; heating the γPNA capture probe, γPNA reporter probes, and the sample; and invading of the γPNA reporter probes to the targeted genomic material, wherein the γPNA reporter probes are used to detect the targeted genomic materials.

In some embodiments, the contacting step is preceded by an amplification step comprising an enzymatic amplification of the of targeted sepsis-related genomic material.

In some embodiments, the genomic material in the clinical specimen is sheared.

In some embodiments, the γPNA capture probes are bound to a support substrate. In some embodiments, a first carbon-linker, comprising of at least three carbons, binds the γPNA capture probes to the support substrate. In some embodiments, the support substrate is selected from the group consisting of: a magnetic bead, a bead, a well, a plate, for example polystyrene microtiter plate, a test tube, a stick, for example a dipstick, plastic, glass, and a chip or biochip. In some embodiments, the support substrate is coated with Avidin, Neutravidin, or Streptavidin.

In some embodiments, the γPNA capture probes and/or γPNA reporter probes comprise one or more functional moiety selected from the group consisting of a binding molecule, a spacer group, a linker group, a hydrophobicity-changing group, a charge-inducing group, and a structural change-inducing group. In some embodiments, the spacer group is selected from the group consisting of: (ethylene) glycol, di(ethylene)glycol, tri(ethylene)glycol, poly(ethylene)glycol, 6-carbon linker, and 12 carbon linker. In some embodiments, the linker group is selected from the group consisting of: COOH group, NHS-ester group, malemide chemistry, Click chemistry, streptavidin, and biotinylation. In some embodiments, the hydrophobicity-changing group is selected from the group consisting of: a naturally polar or charged side group or linker that decreases hydrophobicity, and a naturally apolar and uncharged side group or linker that increases hydrophobicity. In some embodiments, the charge-inducing group is selected from the group consisting of: COOH group, $NH_3$ groups, OH groups, and metallic ions. In some embodiments, the structural change-inducing group induces a chemical modification along the peptide backbone of PNA and is selected from the group consisting of: amino acid-based side chain, nanoparticle, small molecule or intercalating agent. In some embodiments, the γPNA probe comprises biotin or hapten.

In some embodiments, detecting the presence of one or more targeted genomic material is through a signal selected from the group consisting of: fluorescence, luminescence, FRET, colorimetric, calorimetric, interference patterns, pH, resistance/conductivity, enzymatic function and kinetics, protein structure, and electrical potential.

In some embodiments, the γPNA reporter probes comprise a second carbon-linker. In some embodiments, the second carbon-linker comprises of one or more biotinylation sites.

An alternative embodiment provides for a composition for diagnosing sepsis, wherein the composition comprises a γPNA probe composition comprising at least one sequence from one or more of the groups of probes selected from the group consisting of: SEQ ID NOS: 1-18, SEQ ID NOS: 19-22, SEQ ID NOS: 23-28, SEQ ID NOS: 29-34, SEQ ID NOS: 35-38, SEQ ID NOS: 39-57, SEQ ID NOS: 58-72, SEQ ID NOS: 73-91, SEQ ID NOS: 92-94, SEQ ID NOS: 95-97, SEQ ID NOS: 98-110, SEQ ID NOS: 111-113, SEQ ID NOS: 114-117, SEQ ID NOS: 118-119, SEQ ID NOS: 120-121, SEQ ID NOS: 122-153, SEQ ID NOS: 154-166, SEQ ID NOS: 167-190, SEQ ID NOS: 191-193, SEQ ID NOS: 194-196, SEQ ID NOS: 197-211, SEQ ID NOS: 212-215, SEQ ID NOS: 216-230, SEQ ID NOS: 231-248, SEQ ID NOS: 249-309, complementary sequence thereof, and functional equivalents thereof.

In some embodiments, the γPNA probe comprises a support substrate. In some embodiments, the support substrate is selected from the group consisting of: a magnetic bead, a bead, a well, a plate, for example polystyrene microtiter plate, a test tube, a stick, for example a dipstick, plastic, glass, and a chip or biochip. In some embodiments, the support substrate is coated with Avidin, Neutravidin, or Streptavidin.

In some embodiments, the γPNA probe comprises one or more functional moiety selected from the group consisting of a binding molecule, a spacer group, a linker group, a hydrophobicity-changing group, a charge-inducing group, and a structural change-inducing group.

In some embodiments, the γPNA probe emits a detectable signal selected from the group consisting of: fluorescence, luminescence, FRET, colorimetric, calorimetric, interference patterns, pH, resistance/conductivity, enzymatic function and kinetics, protein structure, and electrical potential.

In some embodiments, the γPNA probe comprises a carbon-linker comprising at least three carbons. In some embodiments, the carbon-linker comprises of one or more biotinylation sites.

An alternative embodiment provides for a kit for detecting sepsis comprising a γPNA capture probe composition comprising at least one sequence from one or more of the groups of probes selected from the group consisting of: SEQ ID NOS: 1-18, SEQ ID NOS: 19-22, SEQ ID NOS: 23-28, SEQ ID NOS: 29-34, SEQ ID NOS: 35-38, SEQ ID NOS: 39-57, SEQ ID NOS: 58-72, SEQ ID NOS: 73-91, SEQ ID NOS: 92-94, SEQ ID NOS: 95-97, SEQ ID NOS: 98-110, SEQ ID NOS: 111-113, SEQ ID NOS: 114-117, SEQ ID NOS: 118-119, SEQ ID NOS: 120-121, SEQ ID NOS: 122-153, SEQ ID NOS: 154-166, SEQ ID NOS: 167-190, SEQ ID NOS: 191-193, SEQ ID NOS: 194-196, SEQ ID NOS: 197-211, SEQ ID NOS: 212-215, SEQ ID NOS: 216-230, complementary sequence thereof, and functional equivalents thereof.

In some embodiments, the kit comprises a γPNA reporter probe composition comprising at least one sequence from one or both of the groups of reporter probes: SEQ ID NOS: 231-248 and SEQ ID NOS: 249-309, complementary sequence thereof, and functional equivalents thereof.

In some embodiments, the γPNA capture probes are bound to a support substrate. In some embodiments, the support substrate is selected from the group consisting of: a magnetic bead, a bead, a well, a plate, for example polystyrene microtiter plate, a test tube, a stick, for example a dipstick, plastic, glass, and a chip or biochip. In some embodiments, the support substrate is coated with Avidin, Neutravidin, or Streptavidin.

In some embodiments, the γPNA probe composition emits a detectable signal selected from the group consisting of: fluorescence, luminescence, FRET, colorimetric, calorimetric, interference patterns, pH, resistance/conductivity, enzymatic function and kinetics, protein structure, and electrical potential.

Another alternative embodiment provides for a method for diagnosing sepsis comprising contacting a plurality of γPNA reporter probes to genomic material in a clinical sample obtained from a subject suspected of having sepsis, wherein the γPNA reporter probes comprise at least one sequence from one or both of the groups of reporter probes: SEQ ID NOS: 231-248 and SEQ ID NOS: 249-309, complementary sequence thereof, and functional equivalents thereof; heating the γPNA reporter probes and the sample; invading a plurality of targeted sepsis-related genomic material by the γPNA reporter probes; contacting the plurality of sepsis-related genomic material with γPNA capture probes, wherein the γPNA capture probes comprise at least one sequence from one or more of the groups of probes selected from the group consisting of: SEQ ID NOS: 1-18, SEQ ID NOS: 19-22, SEQ ID NOS: 23-28, SEQ ID NOS: 29-34, SEQ ID NOS: 35-38, SEQ ID NOS: 39-57, SEQ ID NOS: 58-72, SEQ ID NOS: 73-91, SEQ ID NOS: 92-94, SEQ ID NOS: 95-97, SEQ ID NOS: 98-110, SEQ ID NOS: 111-113, SEQ ID NOS: 114-117, SEQ ID NOS: 118-119, SEQ ID NOS: 120-121, SEQ ID NOS: 122-153, SEQ ID NOS: 154-166, SEQ ID NOS: 167-190, SEQ ID NOS: 191-193, SEQ ID NOS: 194-196, SEQ ID NOS: 197-211, SEQ ID NOS: 212-215, SEQ ID NOS: 216-230, complementary sequence thereof, and functional equivalents thereof; heating the γPNA reporter probes, the γPNA capture probes, and the sample; invading the plurality of targeted sepsis-related genomic material by the γPNA capture probes; and detecting a presence of one or more targeted genomic material, wherein detection of the presence of target genomic material is indicative of sepsis infection.

In some embodiments, the support substrate is selected from the group consisting of: a magnetic bead, a bead, a well, a plate, for example polystyrene microtiter plate, a test tube, a stick, for example a dipstick, plastic, glass, and a chip or biochip. In some embodiments, the support substrate is coated with Avidin, Neutravidin, or Streptavidin.

In some embodiments, wherein the γPNA capture probes and γPNA reporter probes comprise one or more functional moiety selected from the group consisting of: a binding molecule, a spacer group, a linker group, a hydrophobicity-changing group, a charge-inducing group, and a structural change-inducing group.

In some embodiments, the γPNA capture probes and γPNA reporter probes comprise biotin or hapten.

In some embodiments, the γPNA reporter probes emit a detectable signal selected from the group consisting of: fluorescence, luminescence, FRET, colorimetric, calorimetric, interference patterns, pH, resistance/conductivity, enzymatic function and kinetics, protein structure, and electrical potential.

DETAILED DESCRIPTION

Figure 1A:
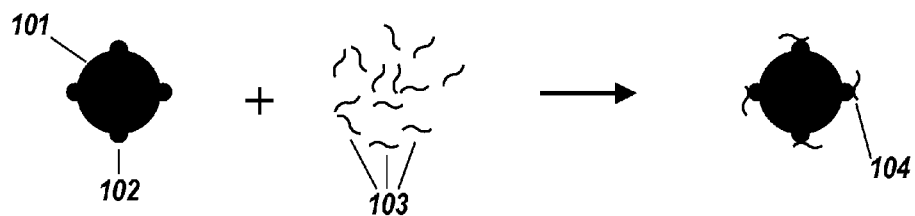
FIG. 1A is a schematic of γPNA capture probes binding to a magnetic bead that is coated with neutravidin.

It is to be appreciated that certain aspects, modes, embodiments, variations and features of the invention are described below in various levels of detail in order to provide a substantial understanding of the present invention. The definitions of certain terms as used in this specification are provided below. Unless defined otherwise, all technical and scientific terms used herein generally have the same meaning as commonly understood by one of ordinary skill in the art to which this invention belongs. As used herein the following terms have the following meanings.

DEFINITIONS

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope as described herein.

The term "about" when used before a numerical designation, e.g., temperature, time, amount, and concentration, including range, indicates approximations which may vary by (+) or (−) 10%, 5%, or 1%.

As used in this specification and the appended claims, the singular forms "a", "an" and "the" include plural referents unless the content clearly dictates otherwise. For example, reference to "a cell" includes a combination of two or more cells, and the like.

As used herein, "sample" refers to blood samples, culture samples, or DNA samples that originate from or are generated from a person or patient that is suspected of having sepsis. The samples taken or derived from the person or patient are believed to contain pathogenic genomic material related to sepsis. Additionally, sample can refer to mixture of genomic material that is to be tested for the presence sepsis related pathogenic materials.

As used herein, "pathogenic or bacterial genomic material" or "targeted sepsis-related genomic material" or "targeted genomic material" refer to DNA, RNA, oligonucleotides, or polynucleic acids related to any genus or species of pathogens related to sepsis. Additionally, DNA and RNA are broadly used to include, but not limited to, ribosomal DNA and RNA (rDNA and rRNA), messenger RNA (mRNA), transfer DNA (tDNA), and mitochondrial DNA (mDNA). Examples of such pathogens include, but are not limited to, *Staphylococcus epidermis*, *Staphylococcus aureus*, *Enterococcus faecalis*, *Enterococcus faecium*, and *Escherichia coli*.

As used herein, "support substrate" refers a solid substrate upon which γPNAs can be immobilized. In one embodiment, the support substrate is a magnetic bead, a bead, a well, a plate, for example polystyrene microtiter plate, a test tube, a stick, for example a dipstick, plastic, glass, and a chip or biochip. In some embodiments, the support substrate is silicon based or coated with either a semiconductive, conductive, or insulating material. In some embodiments, the support substrate includes metallic surfaces that are functionalized. In other embodiments the solid substrate may be manufactured from polymers, nylon, nitrocellulose, polyacrylamide, oxides. In some embodiments, the solid support is manufactured from multiple materials. In some embodiments, the surface of the support substrate is coated with an aminosilane or any other commonly known surface treatments, such as epoxysilanes.

As used herein, "immobilizing" describes binding of γPNA capture probes onto a solid, support substrate prior to the introduction of a sample. Immobilization of the γPNA capture probes sequences on a support substrate can be achieved through various means such as covalent binding protocols or non-covalent binding protocols. Binding modalities and chemistries are commonly known to those skilled in the art.

As used herein, "signal" refers to that which is detectable though optical modalities, or through electrical modalities, or through biological modalities, or through chemical modalities.

As used herein, "diagnosis" refers to determining or identifying the presence or absence of one or more sepsis-inducing pathogen in a patient. Additionally, diagnosis can also refer to determining a patient's susceptibility to sepsis.

As used herein, "washing" refers to steps to remove unwanted, unbound, weakly bound, non-specifically bound genomic and other non-genomic material from the vicinity of the PNA probe. Washing steps are well established within the field and have been optimized for numerous biological assays such as ELISA, Western blot assays, Southern blot assays, Northern Blot assays, DNA microarrays, RNA microarrays, protein microarrays, and LiPA. Washing steps, and optimizing of the washing steps are well established and known to those skilled in the art.

The term "invasion" or "invade" refers to γPNA probes, both capture and reporter, binding to target sequences using either natural or induced structural fluctuations, referred to as DNA breathing or DNA bubbles. Nucleic acids may, on occasion, present their nucleobases to the bulk, meaning the nucleobases are not hidden within the structure. When this occurs, the γPNA, may bind to those exposed nucleobases through typical Watson Crick base-pairing rules. Upon the closure of this DNA bubble, the γPNA remains bound to the nucleic acid region effectively displacing, locally, the complementary nucleic acid strand—hence γPNA invades the nucleic acid structure locally.

Culture-free diagnostic tools are required for the timely and proper treatment of microbial pathogens which induce a septic response in afflicted patients. While recent advances in molecular diagnostics have revolutionized numerous disease areas in clinical testing, severe technical limitations prevent molecular techniques from having significant impact in cases of bacteremia or fungemia. Identification of the infecting pathogen and its susceptibility to antimicrobial therapy still require a time-intensive step of culturing. Thus, the realities of sepsis remain grim; a mortality rate of 28% with 210,000 annual deaths in the U.S. alone. The present disclosure describes compounds, methods, and kits related to a culture-free approach to sepsis pathogen identification and susceptibility analysis.

Peptide Nucleic Acid

Peptide nucleic acids (PNAs) are synthetic, or non-naturally, occurring oligomers, which have displayed the ability to bind to both DNA and RNA according to either Watson-Crick and/or Hoogstgein base pairing. In PNA, the negatively charged sugar-phosphate backbone of natural DNA or RNA has been replaced with a neutral peptide backbone. PNA's neutral backbone negates the energy penalty natural probes must expend to overcome the mutual repulsion of their negatively charged phosphate backbone. Thus, PNA binds to nucleic acids (NAs) with much greater affinities than natural probes. Other advantages of PNAs in general include: the ability to bind to both natural and synthetic targets, fast binding kinetics, and the ability to add chemical moieties such as, but not limited to, fluorescent dyes, biotin, protein binding agents, radio-labeling, or quantum dots.

A new class of PNA, termed γPNA, is PNA with a simple backbone modification at the γ-position of the N-(2-aminoethyl) glycine backbone that generates a chiral center. In an unbound state, the configuration of ordinary PNA or DNA probes is a random, globular structure. In contrast, unbound γPNA probes assume a right-handed helix structure, pre-organized for Watson-Crick base pairing, which greatly facilitating binding.

γPNA probes have several major advantages of over natural DNA probes and ordinary PNA probes. Some of the advantages include:

1) γPNA has substantially greater affinity to nucleic acids than other natural or synthetic probes. Typical Tm values for γPNA/DNA 15 bp hybrids are ~20° C. higher (Tm>95° C.) than equivalent ordinary PNA/DNA hybrids and −50° C. higher than natural dsDNA. γPNA Kd values are even comparable to antibodies (nM-pM).

2) γPNA is significantly more sequence specific. Ordinary PNAs are commonly used as primer clamps to overcome the poor sequence specificity of natural DNA by removing the likelihood of PCR beacons binding to slightly mismatched regions. γPNAs have even greater sequence specificity than ordinary PNAs, as reflected in the greater increase in ΔTm when a mismatch is induced.

3) γPNA has the unique ability to invade structured nucleic acids, such as double stranded DNA (dsDNA) and RNA, which facilitates a less complex method for target identification. γPNA's affinity to single-stranded NAs is so high that it has the ability to naturally invade the double stranded structure and bind through standard Watson-Crick base pairing to the correct sequence. Binding to single-stranded NAs occurs just as it would for other synthetic and natural nucleic acid probes.

PNA Targets and Sequences

Comparative analysis of ribosomal DNA (rDNA) sequences has become a well-established method for establishing phylogenetic relationships between microbial species. Microbial rDNA are among the most highly conserved and most rigorously studied regions in a microbial genome. Minute differences in rDNA sequences enable the design of highly specific probes for target regions, which are specific to one or more pathogens.

Polymicrobial infections are problematic in that numerous pathogens with their own inherent resistance traits induce similar pathophysiological traits in the host during sepsis. Despite the similarity in host response and the high similarity at the genomic level of numerous pathogens; treatment regimens could vary significantly depending on species traits as well as the presence or absence of genes which encode for antimicrobial resistance.

Sequence analysis for specific genes that might encode for a resistance to a particular antimicrobial compound has likewise been established. Multiple regions in these genes are highly conserved and can be used to create markers for targeting. The targeting the highly conserved regions would enable the detection of a gene sequence that encodes for antimicrobial resistance.

The γPNA probes preferably target rDNA/rRNA sequence of the microbial pathogen. In the present disclosure, the γPNA probe sequences all relate to identifying bacterium involved in sepsis. Tables 1-25 describes a non-exclusive list of sequences capable of identifying bacterium involved with sepsis. Since the γPNA probes will bind to dsDNA, one skilled in the art would know that the reverse-complementary sequences of the sequences in Tables 1-25 can also be γPNA probe sequences. Thus, in some embodiments, the target sequence may be the reverse-complementary sequence to those identified here.

In some embodiments, γPNA probe sequences are those which will bind to the corresponding rDNA/rRNA target sequences through Watson-Crick base-pairing. Additional base-pairing methods such as Hoogstein have been demonstrated with other PNA variants (such as bis-PNA).

Since PNAs do not have phosphate-sugar backbone, orientation is guided by the terminus of the peptide backbone for proper binding. Therefore, the C-terminus aligns with the 5' end of the DNA/RNA target, and the N-terminus aligns with the 3' end of the DNA/RNA target.

In addition to the natural nucleobases, the inclusion of modified or synthetic nucleobases may also be included to enhance γPNA characteristics. A common synthetic nucleobase for use with γPNA is typically called the 'G-clamp' which refers to a pseudo-cytosine (9-(2-guanidinoethoxy) phenoxazine). Another common synthetic nucleobase used in PNAs is the J-base which carries a hydrogen atom at the N3 position allowing its Hoogsteen pairing with a guanine base without protonation.

TABLE 1

γPNA capture probe sequences for *Staphylococcus aureus*

| SEQ ID | Sequence (N-terminus to C-terminus) |
|---|---|
| SEQ ID NO: 1 | CGG AAC ATC TTC TTC |
| SEQ ID NO: 2 | TCA GAA GAT GCG GAA |
| SEQ ID NO: 3 | CCT GAT AAG CGT GAG |
| SEQ ID NO: 4 | GAG TCC ACT TAG GCC |
| SEQ ID NO: 5 | CAC TTA GGC CCA CCA |
| SEQ ID NO: 6 | AGG CCC ACC ATT ATT |
| SEQ ID NO: 7 | AAC GGA CGA GAA GCT |
| SEQ ID NO: 8 | TCC TTT GAC AAC TCT |
| SEQ ID NO: 9 | AAC GGA CGA GAA GCT |
| SEQ ID NO: 10 | AGA GAT AGA GCC TTC |
| SEQ ID NO: 11 | TTT GAC AAC TCT AGA |

TABLE 1-continued

γPNA capture probe sequences for *Staphylococcus aureus*

| SEQ ID | Sequence (N-terminus to C-terminus) |
|---|---|
| SEQ ID NO: 12 | CTT CTC TGA TGT TAG |
| SEQ ID NO: 13 | GGA TAA TAT TTT GAA |
| SEQ ID NO: 14 | TTC AAA AGT GAA AGA |
| SEQ ID NO: 15 | AGA CGG TCT TGC TGT |
| SEQ ID NO: 16 | ATC CGC GCT GCA TTA |
| SEQ ID NO: 17 | AGA ACA TAT GTG TAA |
| SEQ ID NO: 18 | TAA CCT TTT AGG AGC |

TABLE 2

γPNA capture probe sequences for *Enterococcus faecalis*

| SEQ ID | Sequence (N-terminus to C-terminus) |
|---|---|
| SEQ ID NO: 19 | ACA AGG ACG TTA GTA |
| SEQ ID NO: 20 | CTT TCC TCC CGA GTG |
| SEQ ID NO: 21 | CCT ACC CAT CAG AGG |
| SEQ ID NO: 22 | GGA CGT TAG TAA CTG |

TABLE 3

γPNA capture probe sequences for *Enterococcus faecium*

| SEQ ID | Sequence (N-terminus to C-terminus) |
|---|---|
| SEQ ID NO: 23 | CTT GCT CCA CCG GAA |
| SEQ ID NO: 24 | CTT TTT CCA CCG GAG |
| SEQ ID NO: 25 | ATG GTT TTG ATT TGA |
| SEQ ID NO: 26 | CTT TTT CCA CCG GAG |
| SEQ ID NO: 27 | CGT ATA ACA ATC GAA |
| SEQ ID NO: 28 | CGT ATA ACA ATC AAA |

TABLE 4

γPNA capture probe sequences for *Escherichia coli*

| SEQ ID | Sequence (N-terminus to C-terminus) |
|---|---|
| SEQ ID NO: 29 | AAC AGG AAG AAG CTT |
| SEQ ID NO: 30 | GGA GTA AAG TTA ATA |
| SEQ ID NO: 31 | ATA CCT TTG CTC ATT |
| SEQ ID NO: 32 | CAT CTG ATA CTG GCA |

TABLE 4-continued

γPNA capture probe sequences for *Escherichia coli*

| SEQ ID | Sequence (N-terminus to C-terminus) |
|---|---|
| SEQ ID NO: 33 | TTG CTT CTT TGC TGA |
| SEQ ID NO: 34 | AGC TTG AGT CTC GTA |

TABLE 5

γPNA capture probe sequences for *Staphylococcus epidermidis*

| SEQ ID | Sequence (N-terminus to C-terminus) |
|---|---|
| SEQ ID NO: 35 | GCT CCT CTG ACG TTA |
| SEQ ID NO: 36 | ATA ATA TAT TGA ACC |
| SEQ ID NO: 37 | TTC AAT AGT GAA AGA |
| SEQ ID NO: 38 | AAC TAT GCA CGT CTT |

TABLE 6

γPNA capture probe sequences for *Pseudomonas aeruginosa*

| SEQ ID | Sequence (N-terminus to C-terminus) |
|---|---|
| SEQ ID NO: 39 | GAG CGG ATG AAG GGA |
| SEQ ID NO: 40 | CTT GCT CCT GGA TTC |
| SEQ ID NO: 41 | AAT CTG CCT GGT AGT |
| SEQ ID NO: 42 | ATA ACG TCC GGA AAC |
| SEQ ID NO: 43 | CCG CAT ACG TCC TGA |
| SEQ ID NO: 44 | AGA TGA GCC TAG GTC |
| SEQ ID NO: 45 | GAC GAT CCG TAA CTG |
| SEQ ID NO: 46 | CAG TAA GTT AAT ACC |
| SEQ ID NO: 47 | CAA CAG AAT AAG CAC |
| SEQ ID NO: 48 | TCC AAA ACT ACT GAG |
| SEQ ID NO: 49 | CTG AGC TAG AGT ACG |
| SEQ ID NO: 50 | AAT TTC CTG TGT AGC |
| SEQ ID NO: 51 | GCG TAG ATA TAG GAA |
| SEQ ID NO: 52 | ACC TAG ATA TAG GAA |
| SEQ ID NO: 53 | TGT CGA CTA GCC GTT |
| SEQ ID NO: 54 | AGC CGT TGG GAT CCT |
| SEQ ID NO: 55 | TGA GAT CTT AGT GGC |
| SEQ ID NO: 56 | AAC TCA GAC ACA GGT |
| SEQ ID NO: 57 | TTG TCC TTA GTT ACC |

TABLE 7

γPNA capture probe sequences for *Streptococcus pneumoniae*

| SEQ ID | Sequence (N-terminus to C-terminus) |
|---|---|
| SEQ ID NO: 58 | CTG AAG GAG GAG CTT |
| SEQ ID NO: 59 | AGG AGC TTG CTT CTC |
| SEQ ID NO: 60 | ATG ACA TTT GCT TAA |
| SEQ ID NO: 61 | ACT TGC ATC ACT ACC |
| SEQ ID NO: 62 | AAT GGA CGG AAG TCT |
| SEQ ID NO: 63 | AAG AAC GAG TGT GAG |
| SEQ ID NO: 64 | AAA GTT CAC ACT GTG |
| SEQ ID NO: 65 | TAT CTT ACC AGA AAG |
| SEQ ID NO: 66 | TTA GAT AAG TCT GAA |
| SEQ ID NO: 67 | AAA GGC TGT GGC TTA |
| SEQ ID NO: 68 | TTA ACC ATA GTA GGC |
| SEQ ID NO: 69 | AAA CTG TTT AAC TTG |
| SEQ ID NO: 70 | ACT TGA GTG CAA GAG |
| SEQ ID NO: 71 | TCT CTG GCT TGT AAC |
| SEQ ID NO: 72 | CCT CTG ACC GCT CTA |

TABLE 8

γPNA capture probe sequences for *Streptococcus pyogenes*

| SEQ ID | Sequence (N-terminus to C-terminus) |
|---|---|
| SEQ ID NO: 73 | AGA ACT GGT GCT TGC |
| SEQ ID NO: 74 | CTG GTG CTT GCA CCG |
| SEQ ID NO: 75 | TTG CAC CGG TTC AAG |
| SEQ ID NO: 76 | TAA CCT ACC TCA TAG |
| SEQ ID NO: 77 | ATA AGA GAG ACT AAC |
| SEQ ID NO: 78 | AGA CTA ACG CAT GTT |
| SEQ ID NO: 79 | AGT AAT TTA AAA GGG |
| SEQ ID NO: 80 | AAT TGC TCC ACT ATG |
| SEQ ID NO: 81 | CTC CAC TAT GAG ATG |
| SEQ ID NO: 82 | TTA GAG AAG AAT GAT |
| SEQ ID NO: 83 | GAA AAT CCA CCA AGT |
| SEQ ID NO: 84 | TGA CGG TAA CTA ACC |
| SEQ ID NO: 85 | AAA GGC ATT GGC TCA |
| SEQ ID NO: 86 | CTC AAC CAA TGT ACG |
| SEQ ID NO: 87 | AAA CTG GAG AAC TTG |
| SEQ ID NO: 88 | CTT GAG TGC AGA AGG |
| SEQ ID NO: 89 | GCT TAG TGC CGG AGC |

TABLE 8-continued

γPNA capture probe sequences for *Streptococcus pyogenes*

| SEQ ID | Sequence (N-terminus to C-terminus) |
|---|---|
| SEQ ID NO: 90 | ATA GAG TTT TAC TTC |
| SEQ ID NO: 91 | GGT ACA TCG GTG ACA |

TABLE 9

γPNA capture probe sequences for *Klebsiella pneumonia*

| SEQ ID | Sequence (N-terminus to C-terminus) |
|---|---|
| SEQ ID NO: 92 | AAG GCG ATA AGG TTA |
| SEQ ID NO: 93 | TGC CAG CGG TTA GGC |
| SEQ ID NO: 94 | AAG GCG ATG AGG TTA |

TABLE 10

γPNA capture probe sequences for *Enterobacter* species

| SEQ ID | Sequence (N-terminus to C-terminus) |
|---|---|
| SEQ ID NO: 95 | AAG GCG TTA AGG TTA |
| SEQ ID NO: 96 | ATA ACC TTG GCG ATT |
| SEQ ID NO: 97 | TGC CAG CGG TCC GGC |

TABLE 11

γPNA capture probe sequences for *Proteus mirabilis*

| SEQ ID | Sequence (N-terminus to C-terminus) |
|---|---|
| SEQ ID NO: 98 | AAC AGG AGA AAG CTT |
| SEQ ID NO: 99 | TTT CTT GCT GAC GAG |
| SEQ ID NO: 100 | GGA TCT GCC CGA TAG |
| SEQ ID NO: 101 | ATA ATG TCT ACG GAC |
| SEQ ID NO: 102 | TAC GGA CCA AAG CAG |
| SEQ ID NO: 103 | TTG CAC TAT CGG ATG |
| SEQ ID NO: 104 | CGG ATG AAC CCA TAT |
| SEQ ID NO: 105 | AAT ACC CTT GTC AAT |
| SEQ ID NO: 106 | TCA ATT AAG TCA GAT |
| SEQ ID NO: 107 | ATC TGA AAC TGG TTG |
| SEQ ID NO: 108 | ATT TAG AGG TTG TGG |
| SEQ ID NO: 109 | TTG TGG TCT TGA ACC |
| SEQ ID NO: 110 | AGC GAA TCC TTT AGA |

TABLE 12

γPNA capture probe sequences for *Staphylococcus lugdunensis*

| SEQ ID | Sequence (N-terminus to C-terminus) |
|---|---|
| SEQ ID NO: 111 | GAC TGG GAC AAC TTC |
| SEQ ID NO: 112 | ATA ATA TGT TGA ACC |
| SEQ ID NO: 113 | GTC TTA GGA TCG TAA |

TABLE 13

γPNA capture probe sequences for *Staphylococcus warneri*

| SEQ ID | Sequence (N-terminus to C-terminus) |
|---|---|
| SEQ ID NO: 114 | GGA TAA CAT ATT GAA |
| SEQ ID NO: 115 | AAA GGC GGC TTT GCT |
| SEQ ID NO: 116 | TCT GTT ATC AGG GAA |
| SEQ ID NO: 117 | GTA CCT GAT CAG AAA |

TABLE 14

γPNA capture probe sequences for *Staphylococcus hominis*

| SEQ ID | Sequence (N-terminus to C-terminus) |
|---|---|
| SEQ ID NO: 118 | AGA TGG CTT TGC TAT |
| SEQ ID NO: 119 | GAG ATA GAA GTT TCC |

TABLE 15

γPNA capture probe sequences for *Serratia Marcescens*

| SEQ ID | Sequence (N-terminus to C-terminus) |
|---|---|
| SEQ ID NO: 120 | AAG GTG GTG AGC TTA |
| SEQ ID NO: 121 | TTA ATA CGT TCA TCA |

TABLE 16

γPNA capture probe sequences for *Acinetobacter baumannii*

| SEQ ID | Sequence (N-terminus to C-terminus) |
|---|---|
| SEQ ID NO: 122 | AAG GTA GCT TGC TAC |
| SEQ ID NO: 123 | TTG CTA CCG GAC CTA |
| SEQ ID NO: 124 | AAT GCT TAG GAA TCT |
| SEQ ID NO: 125 | AAT CTG CCT ATT AGT |
| SEQ ID NO: 126 | ACA ACA TCT CGA AAG |
| SEQ ID NO: 127 | AAA GGG ATG CTA ATA |
| SEQ ID NO: 128 | ACC TTG CGC TAA TAG |
| SEQ ID NO: 129 | ATG AGC CTA AGT CGG |
| SEQ ID NO: 130 | CGA TCT GTA GCG GGT |
| SEQ ID NO: 131 | AAC CCT GAT CCA GCC |
| SEQ ID NO: 132 | AGG CTA CTT TAG TTA |
| SEQ ID NO: 133 | TTT AGT TAA TAC CTA |
| SEQ ID NO: 134 | TAC CTA GAG ATA GTG |
| SEQ ID NO: 135 | ATA GTG GAC GTT ACT |
| SEQ ID NO: 136 | CAG CCA TCT GGC CTA |
| SEQ ID NO: 137 | GCC TAA TAC TGA CGC |
| SEQ ID NO: 138 | TCT ACT AGC CGT TGG |
| SEQ ID NO: 139 | CCT TTG AGG CTT TAG |
| SEQ ID NO: 140 | CGA TAA GTA GAC CGC |
| SEQ ID NO: 141 | GTC GCA AGA CTA AAA |
| SEQ ID NO: 142 | TGG CCT TGA CAT ACT |
| SEQ ID NO: 143 | ATA CTA GAA ACT TTC |
| SEQ ID NO: 144 | AAT CTA GAT ACA GGT |
| SEQ ID NO: 145 | TTT TCC TTA CTT GCC |
| SEQ ID NO: 146 | CCA GCA TTT CGG ATG |
| SEQ ID NO: 147 | ACT TTA AGG ATA CTG |
| SEQ ID NO: 148 | TTG CTA CAC AGC GAT |
| SEQ ID NO: 149 | ATG TGA TGC TAA TCT |
| SEQ ID NO: 150 | TAA TCT CAA AAA GCC |
| SEQ ID NO: 151 | AAG CCG ATC GTA GTC |
| SEQ ID NO: 152 | AAT GCC GCG GTG AAT |
| SEQ ID NO: 153 | TAG CCT AAC TGC AAA |

TABLE 17

γPNA capture probe sequences for *Stenotrophomonas maltophilia*

| SEQ ID | Sequence (N-terminus to C-terminus) |
|---|---|
| SEQ ID NO: 154 | AAC GGC AGC ACA GTA |
| SEQ ID NO: 155 | TAA GAG CTT GCT CTT |
| SEQ ID NO: 156 | GAA TAC ATC GGA ATC |
| SEQ ID NO: 157 | AAA CTT ACG CTA ATA |
| SEQ ID NO: 158 | ATC CAG CTG GTT AAT |
| SEQ ID NO: 159 | GTA CCC AAA GAA TAA |

TABLE 17-continued

γPNA capture probe sequences for *Stenotrophomonas maltophilia*

| SEQ ID | Sequence (N-terminus to C-terminus) |
|---|---|
| SEQ ID NO: 160 | TTG TTT AAG TCT GTT |
| SEQ ID NO: 161 | AGC TAC CTG GAC CAA |
| SEQ ID NO: 162 | TGC AAT TTG GCA CGC |
| SEQ ID NO: 163 | AAC GCG TTA AGT TCG |
| SEQ ID NO: 164 | CTG CAA GCC GGC GAC |
| SEQ ID NO: 165 | AGA AAC CCT ATC TCA |
| SEQ ID NO: 166 | AGC ATT GCT GCG GTG |

TABLE 18

γPNA capture probe sequences for Capture Coagulase-negative *staphylococci* (CoNS).

| Pool # | SEQ ID | Sequence (N-terminus to C-terminus) |
|---|---|---|
| 1 | SEQ ID NO: 167 | AAC AGA TAA GGA GCT |
|   | SEQ ID NO: 168 | AAC AGA CGA GGA GCT |
|   | SEQ ID NO: 169 | AAC AGA CAA GGA GCT |
| 2 | SEQ ID NO: 170 | CTC CTT TGA CGT TAG |
|   | SEQ ID NO: 171 | CTC CTC TGA CGT TAG |
|   | SEQ ID NO: 172 | CTC TTT TGA CGT TAG |
|   | SEQ ID NO: 173 | CTT CTC TGA CGT TAG |
| 3 | SEQ ID NO: 174 | GGA TAA TAT TTC GAA |
|   | SEQ ID NO: 175 | GGA TAA CAT ATT GAA |
|   | SEQ ID NO: 176 | GGA TAA TAT ATT GAA |
|   | SEQ ID NO: 177 | GGA TAA TAT GTT GAA |
| 4 | SEQ ID NO: 178 | AGA TGG TTT TGC TAT |
|   | SEQ ID NO: 179 | AGG CGG CTT TGC TGT |
|   | SEQ ID NO: 180 | AGA CGG TTT TGC TGT |
|   | SEQ ID NO: 181 | AGA TGG CTT TGC TAT |
| 5 | SEQ ID NO: 182 | ACC CGC GCC GTA TTA |
|   | SEQ ID NO: 183 | ACC TGC GCC GTA TTA |
|   | SEQ ID NO: 184 | ATC CGC GCC GTA TTA |
|   | SEQ ID NO: 185 | ATC CGC GCC GCA TTA |
| 6 | SEQ ID NO: 186 | AGA ACA TAC GTG TAA |
|   | SEQ ID NO: 187 | AGA ACA AAC GTG TAA |
|   | SEQ ID NO: 188 | AGA ACA AAT GTG TAA |
| 7 | SEQ ID NO: 189 | TAA CCA TTT GGA GCT |
|   | SEQ ID NO: 190 | TAA CCA TTT ATG GAG |

TABLE 19

γPNA capture probe sequences for *Candida tropicalis*

| SEQ ID | Sequence (N-terminus to C-terminus) |
|---|---|
| SEQ ID NO: 191 | AAT GTC TTC GGA CTC |
| SEQ ID NO: 192 | CAT CTT TCT GAT GCG |
| SEQ ID NO: 193 | GGC TAG CCT TTT GGC |

TABLE 20

γPNA capture probe sequences for *Candida parapsilosis*

| SEQ ID | Sequence (N-terminus to C-terminus) |
|---|---|
| SEQ ID NO: 194 | ATC TTT TTT GAT GCG |
| SEQ ID NO: 195 | TGG CTA GCC TTT TTG |
| SEQ ID NO: 196 | TAT TCA GTA GTC AGA |

TABLE 21

γPNA capture probe sequences for *Candida glabrata*

| SEQ ID | Sequence (N-terminus to C-terminus) |
|---|---|
| SEQ ID NO: 197 | CTT TAC TAC ATG GTA |
| SEQ ID NO: 198 | ATG GTA TAA CTG TGG |
| SEQ ID NO: 199 | ATG CTT AAA ATC TCG |
| SEQ ID NO: 200 | TCC GAT TTT TTC GTG |
| SEQ ID NO: 201 | TGT ACT GGA ATG CAC |
| SEQ ID NO: 202 | AAC CCC AAG TCC TTG |
| SEQ ID NO: 203 | TTG TGG CTT GGC GGC |
| SEQ ID NO: 204 | ACG TTT GGT TCT ATT |
| SEQ ID NO: 205 | TAT TCA ATT GTC AGA |
| SEQ ID NO: 206 | TGT TTT TTT AGT GAC |
| SEQ ID NO: 207 | TAA ATA GTG GTG CTA |
| SEQ ID NO: 208 | ATT TGC TGG TTG TCC |
| SEQ ID NO: 209 | TAT CGG TTT CAA GCC |
| SEQ ID NO: 210 | AGC GAG TCT AAC CTT |
| SEQ ID NO: 211 | TCT TGG TAA TCT TGT |

TABLE 22

γPNA capture probe sequences for *Candida albicans*

| SEQ ID | Sequence (N-terminus to C-terminus) |
|---|---|
| SEQ ID NO: 212 | TTC TGG GTA GCC ATT |
| SEQ ID NO: 213 | GCC ATT TAT GGC GAA |

TABLE 22-continued

γPNA capture probe sequences for *Candida albicans*

| SEQ ID | Sequence (N-terminus to C-terminus) |
| --- | --- |
| SEQ ID NO: 214 | GGT AGC CAT TTA TGG |
| SEQ ID NO: 215 | CTA TCG ACT TCA AGT |

TABLE 23

γPNA capture probe sequences for *Aspergillus* species

| SEQ ID | Sequence (N-terminus to C-terminus) |
| --- | --- |
| SEQ ID NO: 216 | TAC CTT ACT ACA TGG |
| SEQ ID NO: 217 | ACT ACA TGG ATA CCT |
| SEQ ID NO: 218 | TGC TAA AAA CCT CGA |
| SEQ ID NO: 219 | TAA AAA CCA AAT GCC |
| SEQ ID NO: 220 | TAA CGA ATC GCA TGG |
| SEQ ID NO: 221 | TAC CAT GGT GGC AAC |
| SEQ ID NO: 222 | AAT CTA ATC CCC TTA |
| SEQ ID NO: 223 | AGT ACT GGT CCG GCT |
| SEQ ID NO: 224 | GAA CCT CAT GGC CTT |
| SEQ ID NO: 225 | GCC TTC ACT GGC TGT |
| SEQ ID NO: 226 | TTT CTA TGA TGA CCC |
| SEQ ID NO: 227 | TCG GCC CTT AAA TAG |
| SEQ ID NO: 228 | GAG TAC ATC ACC TTG |
| SEQ ID NO: 229 | CTT GTT AAA CCC TGT |
| SEQ ID NO: 230 | AGC TCG TGC CGA TTA |

TABLE 24

γPNA reporter probe sequences for bacteria

| SEQ ID | Sequence (N-terminus to C-terminus) |
| --- | --- |
| SEQ ID NO: 231 | GGA CTA CCA GGG TAT |
| SEQ ID NO: 232 | ACC AGG GTA TCT AAT |
| SEQ ID NO: 233 | CGG GAA CGT ATT CAC |
| SEQ ID NO: 234 | CAG CAG CCG CGG TAA |
| SEQ ID NO: 235 | ATG TGG TTT AAT TCG |
| SEQ ID NO: 236 | GT GCC AGC AGC CGC |
| SEQ ID NO: 237 | AAC GAG CGC AAC CC |
| SEQ ID NO: 238 | GTG GTT TAA TTC GA |
| SEQ ID NO: 239 | ACC TTG TTA CGA CTT |
| SEQ ID NO: 240 | CGA CAG AGT TTG ATC |

TABLE 24-continued

γPNA reporter probe sequences for bacteria

| SEQ ID | Sequence (N-terminus to C-terminus) |
| --- | --- |
| SEQ ID NO: 241 | ACC TTG TTA CGA CTT |
| SEQ ID NO: 242 | CAG CCG CGG TAA TAC |
| SEQ ID NO: 243 | AAC AGG ATT AGA TAC |
| SEQ ID NO: 244 | GTC GTC AGC TCG TGT |
| SEQ ID NO: 245 | ATG TTG GGT TAA GTC |
| SEQ ID NO: 246 | GAA TCG CTA GTA ATC |
| SEQ ID NO: 247 | CTT GTA CAC ACC GCC |
| SEQ ID NO: 248 | GGA CTA CCA GGG TAT CTA AT |

TABLE 25

γPNA reporter probe sequences for fungi

| SEQ ID | Sequence (N-terminus to C-terminus) |
| --- | --- |
| SEQ ID NO: 249 | GTG AAA CTG CGA ATG |
| SEQ ID NO: 250 | CTG CGA ATG GCT CAT |
| SEQ ID NO: 251 | GCT CAT TAA ATC AGT |
| SEQ ID NO: 252 | TCA GTT ATC GTT TAT |
| SEQ ID NO: 253 | CGT TTA TTT GAT AGT |
| SEQ ID NO: 254 | TCT AGA GCT AAT ACA |
| SEQ ID NO: 255 | TAG AGC TAA TAC ATG |
| SEQ ID NO: 256 | TGT ATT TAT TAG ATA |
| SEQ ID NO: 257 | TTA TTA GAT AAA AAA |
| SEQ ID NO: 258 | TGG TTC ATT CAA ATT |
| SEQ ID NO: 259 | TTC AAA TTT CTG CCC |
| SEQ ID NO: 260 | CTG CCC TAT CAA CTT |
| SEQ ID NO: 261 | AAC TTT CGA TGG TAG |
| SEQ ID NO: 262 | TCG ATG GTA GGA TAG |
| SEQ ID NO: 263 | AGG GTT CGA TTC CGG |
| SEQ ID NO: 264 | AGC CTG AGA AAC GGC |
| SEQ ID NO: 265 | AGA AAC GGC TAC CAC |
| SEQ ID NO: 266 | CTA CCA CAT CCA AGG |
| SEQ ID NO: 267 | ATC CAA GGA AGG CAG |
| SEQ ID NO: 268 | AAG GCA GCA GGC GCG |
| SEQ ID NO: 269 | AGG CGC GCA AAT TAC |
| SEQ ID NO: 270 | CAA ATT ACC CAA TCC |
| SEQ ID NO: 271 | GAG GTA GTG ACA ATA |
| SEQ ID NO: 272 | GTA ATT GGA ATG AGT |
| SEQ ID NO: 273 | TGG AAT GAG TAC AAT |

TABLE 25-continued

γPNA reporter probe sequences for fungi

| SEQ ID | Sequence (N-terminus to C-terminus) |
|---|---|
| SEQ ID NO: 274 | CCT TAA CGA GGA ACA |
| SEQ ID NO: 275 | CAA GTC TGG TGC CAG |
| SEQ ID NO: 276 | TAA TTC CAG CTC CAA |
| SEQ ID NO: 277 | AGC GTA TAT TAA AGT |
| SEQ ID NO: 278 | TTA AAG TTG TTG CAG |
| SEQ ID NO: 279 | GTT GCA GTT AAA AAG |
| SEQ ID NO: 280 | AGC TCG TAG TTG AAC |
| SEQ ID NO: 281 | AAA TTA GAG TGT TCA |
| SEQ ID NO: 282 | GTG TTC AAA GCA GGC |
| SEQ ID NO: 283 | ATT AGC ATG GAA TAA T |
| SEQ ID NO: 284 | GGT TCT ATT TTG TTG |
| SEQ ID NO: 285 | TGT TGG TTT CTA GGA |
| SEQ ID NO: 286 | GTC AGA GGT GAA ATT |
| SEQ ID NO: 287 | TGA AAT TCT TGG ATT |
| SEQ ID NO: 288 | TGA AGA CTA ACT ACT |
| SEQ ID NO: 289 | TAC TGC GAA AGC ATT |
| SEQ ID NO: 290 | GTT TTC ATT AAT CA |
| SEQ ID NO: 291 | AAC GAA AGT TAG GG |
| SEQ ID NO: 292 | GAT CAG ATA CCG TCG |
| SEQ ID NO: 293 | ACC GTC GTA GTC TTA |
| SEQ ID NO: 294 | TAG TCT TAA CCA TAA |
| SEQ ID NO: 295 | ACC ATA AAC TAT GCC |
| SEQ ID NO: 296 | TAT GCC GACT AGG GAT |
| SEQ ID NO: 297 | TCG GCA CCT TAC GAG |
| SEQ ID NO: 298 | TAC GAG AAA TCA AAG |
| SEQ ID NO: 299 | AGT ATG GTC GCA AGG |
| SEQ ID NO: 300 | GGC TGA AAC TTA AAG |
| SEQ ID NO: 301 | AGC CTG CGG CTT AAT |
| SEQ ID NO: 302 | TTA ATT TGA CTC AAC |
| SEQ ID NO: 303 | AAA CTC ACC AGG TCC A |
| SEQ ID NO: 304 | TGG AGT GAT TTG TCT |
| SEQ ID NO: 305 | TGT CTG CTT AAT TGC GAT |
| SEQ ID NO: 306 | AAC AGG TCT GTG ATG |
| SEQ ID NO: 307 | TGT GAT GCC CTT AGA |
| SEQ ID NO: 308 | GCG CGC TAC ACT GAC |
| SEQ ID NO: 309 | TTG CTC TTC AAC GAG |

The present disclosure provides γPNA probes useful for the timely detection and/or identification of sepsis-inducing pathogens without the need of culturing the clinical specimens. These qualities are specific to the sequences of the optimized probes, however, one of skill in the art would recognize that other molecules with similar sequences could also be used. The γPNA probes provided herein comprise a sequence that shares at least about 60-70% identity with a sequence described in Tables 1-25. In another embodiment, the γPNA probe has a sequence that shares at least about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identity with the sequences of Tables 1-25 or complement thereof. The terms "identity" or "homology" or "similarity" refer to sequence relationships between two γPNA sequences and can be determined by comparing a nucleotide position in each sequence when aligned for purposes of comparison. The term "identity" refers to the degree to which nucleic acids are the same between two sequences. The term "homology" or "similarity" refers to the relatedness of two functionally-equivalent γPNA sequences.

The probe γPNA sequences also include functional fragments of the sequence provided in Tables 1-25 and sequences sharing certain sequence identities with those in Tables 1-25, as described above, provided they function to specifically anneal to and identify sepsis-inducing pathogens. In one aspect, these fragment sequences have 1, 2, 3, 4, 5, or 6 less bases at either or both ends of the original sequences in Tables 1-25. These shorter sequences are also within the scope of the present disclosure.

In addition, the γPNA sequences, including those provided in Tables 1-25 and sequences sharing certain sequence identities with those in Tables 1-25, as described above, can be incorporated into longer sequences, provided they function to specifically anneal to and identify sepsis-inducing pathogens. In one aspect, the longer sequences have 1, 2, 3, 4, 5, 6, 7, 8, 9, or 10 additional bases at either or both ends of the original sequences. These longer sequences are also within the scope of the present disclosure.

The probe γPNA sequences are complementary to the target nucleic acid sequence. The probe γPNA sequences of the disclosure are optimal for identifying numerous strains of a target nucleic acid, e.g., *Staphylococcus aureus*.

Composition of γPNA Probes

In one embodiment, γPNA probes are used in the diagnosis of sepsis. γPNA probes can be divided into two classes, γPNA capture probes and γPNA reporter probes.

PNA Capture Probes

In some embodiments, the γPNA capture probes are used for the capture, immobilization, and affinity purification of pathogenic genomic material from the sample. In some embodiments, the γPNA capture probes are designed such that the probes' sequence binds only to one species of pathogen. In some embodiments, the γPNA capture probes are designed such that the probes' sequence binds to more than one species of pathogen.

If targeted genomic material is present in the sample, the genomic material will be captured and immobilized or bound by the γPNA capture probe. If genomic material is not present; no genomic material will be immobilized or bound by the γPNA capture probe. The capture and affinity purification of the genomic content does not require the entire genomic fragment to be captured. Rather, a small portion of the target genome being captured constitutes the relevant portion of the genome being captured. In one embodiment, the γPNA capture probes comprise of γPNAs having one or more of the probe sequences listed in Tables 1-23.

The γPNA capture probes can be modified by one or more of the characteristics listed below. That is, the γPNA capture probes include, but are not limited to, the following embodiments.

In some embodiments, the γPNA capture probe sequences will be pre-immobilized onto a support substrate prior to introducing the sample to be tested. In some embodiments, a "single γPNA capture probe sequence" will be pre-immobilized onto a predefined location on a support substrate. A "single γPNA capture probe sequence" is defined as only one sequence for a single microbial pathogenic species, which enables identification and quantification of the target pathogen. For example, a single species γPNA probe sequence encompassing only one of the probe sequences in Table 1 to enable capture of *Staphylococcus aureus*.

In another embodiment, "single γPNA capture probe sequence set," all sequences to a single pathogen, can be pre-immobilized onto a predefined location on a support substrate enabling identification and quantification of the target pathogen. "Single γPNA capture probe sequence set" is defined as multiple sequences for a single microbial pathogenic species, which enables identification and quantification of the target pathogen. For example, a single species γPNA capture probe sequence set encompassing two or more of the probe sequences in Table 1 to enable capture of *Staphylococcus aureus*.

In another embodiment, one or more γPNA capture probe sequences for more than one pathogen can be pre-immobilized onto a predefined location on a support substrate with specificity, enabling identification and quantification of the pathogen subset of interest. For example, multiple γPNA capture probe sequences encompassing at least one probe sequence from both Table 1 and Table 2 to enable capture of *Staphylococcus aureus* and *Enterococcus faecalis*.

In some embodiments, the γPNA capture probes sequences in Tables 1-23 include a moiety which enables them to be surface immobilized on a support substrate. Immobilization of the γPNA capture probes sequences on a support substrate can be achieved through various means such as covalent binding protocols or non-covalent binding protocols. Common binding modalities/chemistries that can be used to immobilize the γPNA on the support substrate include, but are not limited to, COOH groups, NHS-ester groups, malemide chemistry, Click chemistry, streptavidin, thiol chemistry, and biotinylation. There are multiple additional methods which are commonly known to those skilled in the art.

In some embodiments the support substrate is coated with Avidin, Neutravidin, or Streptavidin to facilitate the immobilization of the γPNA capture probes sequences.

In some embodiments, the support substrate is one or more of the group consisting of a magnetic bead, a bead, a well, a plate, for example a polystyrene microtiter plate, a test tube, a stick, for example dipstick, a plastic, a glass, and a chip or a biochip. In some embodiments, the support substrate is silicon based or coated with either a semiconductive, conductive, or insulating material. In some embodiments, the support substrate includes metallic surfaces that are functionalized. In other embodiments the solid substrate may be manufactured from polymers, nylon, nitrocellulose, polyacrylamide, oxides. In some embodiments, the solid support is manufactured from multiple materials. In some embodiments, the surface of the support substrate is coated with an aminosilane or any other commonly known surface treatments, such as epoxysilanes.

The γPNA capture probe lengths are considered to be substantially shorter than those typically used in similar applications due to the enhanced affinity of PNA probes in general and γPNA probes in particular when compared to DNA and RNA probes. The enhanced affinity is a result of the neutral backbone and the pre-organization due to the γ-modification. Shorter probes in general are advantageous as they offer superior sequence specificity.

In one embodiment, the γPNA capture probes have relatively short nucleobase sequences, typically 5-30 bases in length. In another embodiment, the γPNA capture probes are 12-27 bases in length. In another embodiment, the γPNA capture probes are 15-24 bases in length. In another embodiment, the γPNA capture probes are 18-21 bases in length.

In some embodiments, the γPNA capture probe may include moieties which add functionality to the probe itself. Examples include, but are not limited to, binding molecules (such as biotin or haptens), spacer groups, linker groups, a hydrophobicity-changing group, a charge-inducing group, and a structural change-inducing group.

Examples of spacer groups include, but are not limited to, (ethylene)glycol, di(ethylene)glycol, tri(ethylene)glycol, poly(ethylene)glycol, 6-carbon linker, and 12 carbon linker.

Examples of linker groups include, but are not limited to, COOH group, NHS-ester group malemide chemistry, Click chemistry, streptavidin, and biotinylation.

Examples of hydrophobicity-changing groups include, but are not limited to, a naturally polar or charged side group or linker that decreases hydrophobicity, such as side groups mimicking those found on Arginine, Histidine, Lysine, Aspartic Acid, Glutamic Acid, Serine, Threonine, Asparagine, and Glutamine, or a naturally apolar and uncharged side group or linker that increases hydrophobicity, such as side groups mimicking those found on Alanine, Valine, Isoleucine, Leucine, Methionine, Phenylalanine, Tyrosine, and Tryptophan.

Examples of charge-inducing groups include, but are not limited to, COOH group, $NH_3$ groups, OH groups, and metallic ions.

Structural change-inducing group induces a chemical modification in the γPNA capture probe's pseudo-peptide backbone to change the overall charge of the PNA. Typical examples include a selection of positively charged or negatively charged amino acids to thereby alter the charge of the γPNA capture probe. In addition, small particles, small molecules, amino acids residues, small proteins or otherwise peptides may be incorporated, or conjugated along the backbone to alter the physical characteristics of the γPNA capture probe, which would serve to either alter the affinity of the molecule or even its sequence specificity. Examples of structural change-inducing groups include, but are not limited to, amino acid-based side chain, nanoparticle, small molecule or intercalating agent.

In some embodiment, the γPNA capture probe has an easily identifiable signal induced at the capture site. Common signals include, but shall not be limited to fluorescence, luminescence, FRET, colorimetric, calorimetric, interference patterns, pH, resistance/conductivity, enzymatic function and kinetics, protein structure, and electrical potential. In some embodiments, detection of the presence of one or more targeted genomic material is selected from electrical, mass spectrometry, and/or precipitate.

γPNA Reporter Probes

The γPNA reporter probe is used to establish the presence, or alternatively the absence, of a targeted pathogen. γPNA reporter probes are designed to bind a conserved sequence region common among all bacteria. The γPNA reporter probe can be introduced regardless of the presence or absence of the captured genomic material. In one embodiment, the γPNA reporter probes comprise of γPNAs having one or more of the probe sequences listed in Tables 24-25. In one embodiment, the purpose of the γPNA reporter probe is to establish the presence of a target pathogen through the presence of pathogenic genomic material at a particular location. In some embodiments, the purpose of the γPNA reporter probe is to quantify the amount of target pathogen through its genomic material at a particular location.

In one embodiment, a single γPNA reporter probe sequence is used that is common, or universal, to the all of the potential targets. In another embodiment, multiple γPNA reporter probe sequences may be used where together, as a group, they are universal to all or some of the potential target pathogenic genomic material. In another embodiment, multiple γPNA reporter probe sequences may be used which may bind to multiple locations along the target genomic material.

The γPNA reporter probe lengths are considered to be substantially shorter than those typically used in similar applications due to the enhanced affinity of PNA probes in general and γPNA probes in particular when compared to DNA and RNA probes. The enhanced affinity is a result of the neutral backbone and the pre-organization due to the γ-modification. Shorter probes in general are advantageous as they offer superior sequence specificity. In some embodiments, the γPNA reporter probes have relatively short nucleobase sequences, typically 5-30 bases in length. In another embodiment the γPNA reporter probes have 12-27 bases in length. In another embodiment, the γPNA capture probes are 15-24 bases in length. In another embodiment, the γPNA capture probes are 18-21 bases in length.

The γPNA reporter probe contains a moiety that induces a signal. In one embodiment, the γPNA reporter probe has a signal inducing capability selected from, but not limited to fluorophores, quantum dots, enzymes, conjugates, small molecules, chromophore, inorganic nanoparticles (such as metals or semiconductors), conjugation enabling modifications, radioisotopes, and luminescent compounds. In some embodiments, the γPNA reporter probe is synthesized with a specific chemical moiety, which later enables the conjugation of a signal inducing compounds. Examples of specific chemical moieties, but not limited to, are COOH groups, NHS-ester groups, malemide chemistry, Click chemistry, streptavidin, and biotinylation.

In some embodiments, the γPNA reporter probe may include moieties which add functionality to the probe itself. Examples include, but are not limited to, binding molecules (such as biotin or haptens), spacer groups, linker groups, a hydrophobicity-changing group, a charge-inducing group, and a structural change-inducing group.

Examples of spacer groups include, but are not limited to, (ethylene)glycol, di(ethylene)glycol, tri(ethylene)glycol, poly(ethylene)glycol, 6-carbon linker, and 12 carbon linker.

Examples of linker groups include, but are not limited to, COOH group, NHS-ester group malemide chemistry, Click chemistry, streptavidin, and biotinylation.

Examples of hydrophobicity-changing groups include, but are not limited to, a naturally polar or charged side group or linker that decreases hydrophobicity, such as Arginine, Histidine, Lysine, Aspartic Acid, Glutamic Acid, Serine, Threonine, Asparagine, and Glutamine, or a naturally apolar and uncharged side group or linker that increases hydrophobicity, such as side groups mimicking those found in Alanine, Valine, Isoleucine, Leucine, Methionine, Phenylalanine, Tyrosine, and Tryptophan.

Examples of charge-inducing groups include, but are not limited to, COOH group, $NH_3$ groups, OH groups, and metallic ions.

Structural change-inducing group induces a chemical modification in the γPNA reporter probe's pseudo-peptide backbone to change the overall charge of the PNA. Typical examples include a selection of positively charged or negatively charged amino acids to thereby alter the charge of the γPNA reporter probe. In addition, small particles, small molecules, amino acids residues, small proteins or otherwise peptides may be incorporated, or conjugated along the backbone to alter the physical characteristics of the γPNA reporter probe, which would serve to either alter the affinity of the molecule or even its sequence specificity. Examples of structural change-inducing groups include, but are not limited to, amino acid-based side chain, nanoparticle, small molecule or intercalating agent.

However, in some embodiments, the γPNA reporter probe is not required. Rather, signal inducing agents such as DNA/RNA intercalating dyes, which can induce signals themselves, can be used. Several different intercalating dyes are known, such as ethidum bromide and SYBR Green. These dyes are well established and usage of them is well known to those skilled in the art.

In some embodiments, where the γPNA reporter probe is not required, a target pathogen may be PCR amplified with one or more of the primers containing fluorophores, quantum dots, enzymes, conjugates, small molecules, chromophore, inorganic nanoparticles (such as metals or semiconductors), conjugation enabling modifications, radioisotopes, and luminescent compounds or with a specific chemical moiety, which later enables the conjugation of a signal inducing compounds. Examples of specific chemical moieties, but not limited to, are COOH groups, NHS-ester groups, malemide chemistry, Click chemistry, streptavidin, and biotinylation. These methods are well established and known to those skilled in the art.

Carbon Linkers and Biotinylation

Carbon linkers serve different purposes depending on which type of γPNA probe they are attached. γPNA capture probe utilize carbon linkers to remove issues due to potential steric hindrance between the surface of the support substrate and pathogenic genomic material.

In one embodiment, the γPNA capture probes' carbon linkers comprises of at least one carbon. In another embodiment, the γPNA capture probes' carbon linkers comprises of 1-100 carbons. In another embodiment, the γPNA capture probes' carbon linkers comprises of 1-50 carbons. In another embodiment, the γPNA capture probes' carbon linkers comprises of 1-25 carbons. In another embodiment, the γPNA capture probes' carbon linkers comprises of 5-15 carbons.

γPNA reporter probe utilizes carbon linkers to eliminate issues of steric hindrance between the γPNA reporter probe and its signaling moiety. In another embodiment, the γPNA reporter probes' carbon linkers comprises of 1-100 carbons. In another embodiment, the γPNA reporter probes' carbon linkers comprises of 1-50 carbons. In another embodiment, the γPNA reporter probes' carbon linkers comprises of 1-25 carbons. In another embodiment, the γPNA reporter probes' carbon linkers comprises of 5-15 carbons.

The signal expressed by γPNA reporter probes can be amplified by having multiple biotinylation sites. In one embodiment, the γPNA reporter probes' carbon-linker comprises of one or more biotinylation sites.

Methods for Diagnosing Sepsis Using γPNA Probes

In another embodiment, γPNA probes provide methods for diagnosing bacterial and fungal pathogens which induce sepsis.

In one embodiment, a γPNA capture probe, comprising one or more of the above mentioned γPNA capture probe compositions, is combined and incubated with a sample from a person who is suspected of having sepsis. During the incubation, the γPNA capture probes will bind any genomic material (dsDNA, ssDNA, or RNA) with the target sequence. In some embodiments, the mixture of γPNA capture probes and sample is heated to facilitate invasion and binding of the γPNA capture probes to target genomic sequences.

In one embodiment, the method may consist of DNA amplification, for example through PCR, of the genomic material in the sample.

In one embodiment, the genomic material in the sample is sheared. "Shearing" refers to shortening dsDNA, ssDNA, or RNA strands. Shearing circumvents issues with DNA/RNA knotting/supercoiling due to the length of the bacterial genomic material. In some embodiments, the genomic material is sheared to at least 10 kbp strands. In some embodiments, the genomic material is sheared to about 10-500 bp. In other embodiments, the genomic material is sheared to 250-2,000 bp. In other embodiments, the genomic material is sheared from 1,000-10,000. In another embodiment, the genomic material is sheared to 5,000-50,000 bp. Shearing is well-known in the art and commercial kits are widely available.

In one embodiment, identification of the absence or presence of a particular microbe through its genomic material requires a binary result of capture or non-capture. In some embodiments, quantification of the load or copy number of pathogenic genomic material present in the sample can be correlated to the number or amount of pathogenic genomic material captured via the γPNA capture probe.

In one embodiment, a wash step is performed after incubation of the γPNA capture probes and patient sample. Washing steps minimize unwanted, unbound, weakly bound, non-specifically bound target and other non-target material from the vicinity of the γPNA capture probes. Washing steps are well established and known to those skilled in the art.

The capture of the genomic content does not enable identification by itself. Rather a detectable signal must be induced at the capture site. In one embodiment, the γPNA capture probe induces a signal upon binding to the target sequence. The induced signal can be selected from, but not limited to, fluorescence, luminescence, FRET, colorimetric, calorimetric, interference patterns, pH, resistance/conductivity, enzymatic function and kinetics, protein structure, and electrical potential.

In alternate embodiment, after the affinity purification of the target genomic material by γPNA capture probe, a γPNA reporter probe, comprising one or more of the above mentioned γPNA reporter probe compositions, is introduced to the system. The γPNA reporter probe "invades" the immobilized target genomic material. In some embodiments the γPNA reporter probe contains a moiety which simplifies detection of a signal. In some embodiments, the γPNA reporter probe is synthesized with such a signal inducing capability, which include, but not limited to: fluorophores, quantum dots, enzymes, fluorescence, FRET, absorption, raman and/or SERS, chemiluminescence, bioluminescence, and scattering.

In some embodiments, the γPNA reporter probe is synthesized with a specific chemical moiety, which later enables the conjugation of a signal inducing compounds. Examples of specific chemical moieties, but not limited to, are: COOH groups, NHS-ester groups, malemide chemistry, Click chemistry, streptavidin, and biotinylation.

In some embodiments, the method of detecting γPNA reporter probe binding to the target is selected from, but not limited to, electrical, mass spectrometry, and/or precipitate.

In some embodiments, a wash step is performed to remove loosely bound γPNA reporter probes. These steps remove unwanted, unbound, weakly bound, non-specifically bound γPNA reporter probes from the system.

In some embodiments, the distance, in base pairs or bases, between the γPNA capture probe and γPNA reporter probe should be optimized to reduce the likelihood of DNA/RNA breakage between the two binding sites. The distance between the two probes should be sufficient such that the invasion process is not hindered. In some embodiments, the probe sites, or target regions, are between about 10 to 100,000 bases apart. In another embodiment, the probe sites, or target regions, are between about 50 to 75,000 bases apart. In another embodiment, the probe sites, or target regions, are between about 100 to 50,000 bases apart. In another embodiment, the probe sites, or target regions, are between about 10,000 to 100,000 bases apart.

In some embodiments, the γPNA capture probes sequences do not identify a specific species, but can identify a group of species. For example, Coagulase-Negative staphylococci (CoNS) encompasses a group of Staphylococci species, which includes, but is not limited to, *Staphylococcus capitis, Staphylococcus cohnii, Staphylococcus epidermidis, Staphylococcus haemolyticus, Staphylococcus hominis, Staphylococcus lugdunensis, Staphylococcus saprophyticus, Staphylococcus warneri, Staphylococcus capitis*. A pool of γPNA capture probe sequences can be used to identify the CoNS group, see Table 18. For example, if the use of Pool 1 generates a positive signal, the signal indicates that one or more of the above CoNS species is present. In some embodiments, the γPNA capture probes sequences are drawn from one or more pools from Table 18.

Kit for Diagnosing Sepsis Using γPNA

In another embodiment, γPNA probes are used in kits for diagnosis or detection of sepsis or determining the quantity of sepsis related genomic material using γPNA. In one embodiment, the kit comprises a plurality of γPNA capture probes, wherein the γPNA capture probes comprise a sequence or the reverse-complementary sequence selected from one or more of the sequences from Tables 1-23. The γPNA capture probes having any of the characteristics or conjugates previously described. In some embodiments, the kit also comprises a plurality of γPNA reporter probes, wherein the γPNA reporter probes comprise a sequence or the reverse-complementary sequence selected from one or more sequences forn Tables 24-25, the γPNA reporter probes having any of the characteristics or conjugates previously described.

EXEMPLIFICATION

The following examples describe embodiments, which are merely illustrative and should not be construed as limiting in any way.

Example 1

Exemplary Overview

The following steps are a general overview of methods and material for one embodiment using γPNA probes to identify bacteria species in a sample.

Step I: Loading Magnetic Beads with Capture Probes

With reference to FIG. 1A, a solution of excess capture probes 103 is incubated with Neutravidin coated 102 magnetic beads 101. The biotinylated γPNA capture probes naturally bind to the Neutravidin coated beads owing to the very high affinity of biotin to Neutravidin, which immobilizes the γPNA capture probes on the magnetic bead 104. After binding capture probes on the beads, excess probes are washed away using magnetic separation.

After rinsing, the beads are washed with solution of free biotin to block the remaining unoccupied sites on the beads.

Figure 1B:
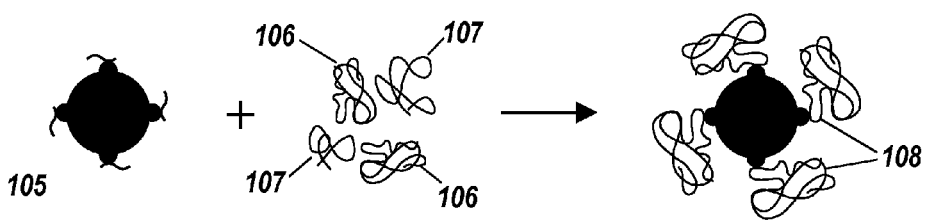
FIG. 1B is a schematic of target genomic materials binding to γPNA capture probes.

Step II: γPNA-Mediated Magnetic Extraction of Species-Specific DNA from a Mixture With reference to FIG. 1B, a clinical sample of a patient with both target DNA genomes 106 and non-targeted DNA genomes 107 is mixed with the magnetic beads with bound γPNA capture probes 105 and heated at 50° C. The γPNA capture probes capture and immobilize the specific species target onto the bead 108, if and only if the corresponding sequence is present in the sample. Extraction of the target DNA is then accomplished by magnetically capturing the beads, and washing away the un-captured background DNA.

Step III: Binding of γPNA Reporter Probes onto the Affinity Purified Targets

Figure 1C:
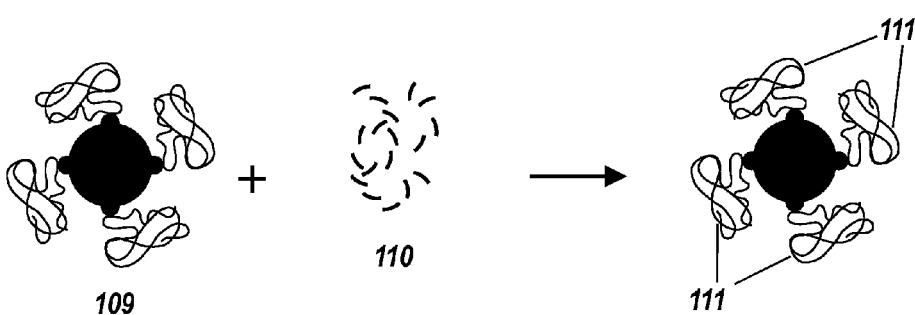
FIG. 1C is a schematic of γPNA reporter probes binding to immobilized target genomic materials.

With reference to FIG. 1C, the magnetic beads with bound target DNA 109 are re-suspended in a 50° C. solution with a large excess of the γPNA reporter probes 110. After γPNA reporter probes bind to the target 111, magnetic separation is used to wash away unbound γPNA reporter probes. If no target was present in the original sample, then no reporter probes will remain in this step. Each probe is specific to a particular pathogen of interest, but is designed to bind a conserved sequence region, independent of the pathogen's subtypes.

Step IV: Binding of Reporter Enzyme onto Captured Targets

Figure 1D:
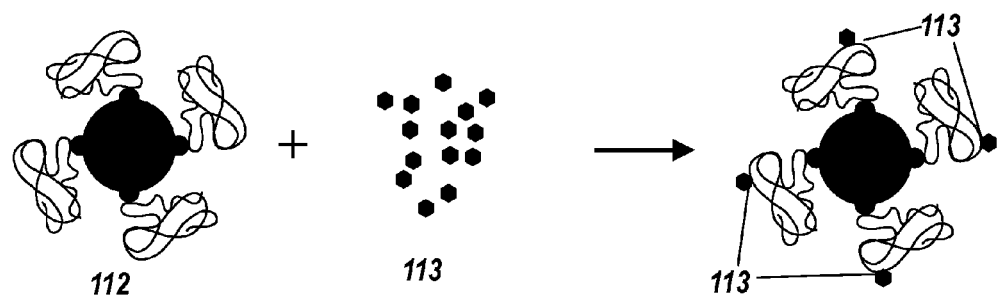
FIG. 1D is a schematic of reporter enzyme conjugates binding to γPNA reporter probes.

With reference to FIG. 1D, a commercial Neutravidin HRP conjugate (ThermoScientific) 113 is mixed with the magnetic beads, which have bound target DNA labeled with γPNA reporter probes 112. The HRP conjugate binds to the biotinylated γPNA reporter probe 114. Unbound enzymes are rinsed away using magnetic separation.

Step V: Reporter Substrate Addition and Optical Readout

Figure 1E:
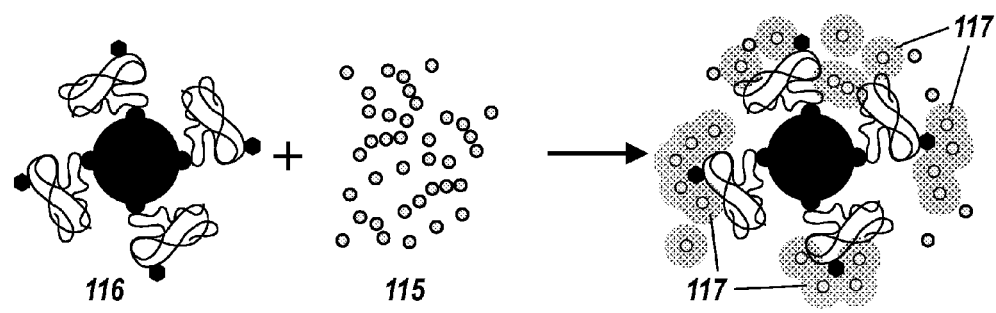
FIG. 1E is a schematic of adding enzyme substrate to induce a signal.

With reference to FIG. 1E, a chemiluminescent HRP substrate 116 from a commercial ELISA kit (SuperSignal ELISA Femto, ThermoScientific) is mixed with the magnetic beads, which contain HRP conjugates 115. The HRP substrate is used to produce light signals indicating 117 the presence of a target in a sample.

Additional optical methods of detection include, but are not limited to, fluorescence, FRET, quantum dots, absorption, raman and/or SERS, chemiluminescence, bioluminescence, and scattering. Other detection methods include, but are not limited to, mass spectrometry and/or precipitate. Support substrates include but are not limited to any well based, dipstick, flow methods, chip, glass, bead, silicon, fibers, and/or paper.

Example 2

Identification of *Staphylococcus aureus* from a Clinical Sample

*Staphylococcus aureus* is detected in a clinical sample by adding the sample to a well or wells on a 96-well microplate, wherein each well is coated with γPNA capture probes specific to *Staphylococcus aureus*. If *Staphylococcus aureus* is present in the sample, a signal is detected that indicates possible sepsis infection in the patient. In an alternative embodiment, positive and negative control samples are also tested along with the clinical sample. The positive and negative control samples are also added to wells coated with γPNA capture probes specific to *Staphylococcus aureus*. The positive control is a sample known to have *Staphylococcus aureus*. The negative control sample is known not to have *Staphylococcus aureus*.

Materials and Methods

Streptavidin coated wells in 96-well microplates (Kaivogen Oy, Finland) are used as a solid support substrate. The microplate is pre-activated with γPNA capture probe(s), wherein the sequence of each capture probe is selected from one or more sequences from Table 1, which are sequences specific to *Staphylococcus aureus*. γPNA capture probes are synthesized (PNA Innovations, Inc., USA) to contain a biotin moiety on its N-terminus, which enables binding of the γPNA capture probes to the microplate well. Post-binding, the well is blocked with a biotin wash, which saturates all remaining biotin binding sites in the well. Post-blocking, the wells are thoroughly rinsed with a 0.2 micron filtered 10 mM NaPi buffer (pH 7.0).

DNA from a clinical patient sample are isolated using a Wizard Genomic Extraction Kit (Promega, Inc., USA). After DNA isolation, the DNA is sheared to a uniform length such as 10 kbp using a 'G-Tube' (Covaris, Inc. USA). Typical shearing protocol includes centrifuging extracted DNA sample for 60 sec at 8 krpm in an Eppendorf Minispin microcentrifuge (Eppendorf AG, Germany). Next, the DNA sample is concentrated and added to the γPNA capture probe-activated well. To promote γPNA capture probe invasion into the genomic target the well is heated to 60° C. for 30 minutes in 10 mM NaPi (pH 7.0) with 15 mM NaCl, 0.05% Tween-20. After invasion, the sample is washed to remove uncaptured DNA from the well. After the wash, γPNA reporter probes, which can also be biotinylated, are added to the well in 10 mM NaPi (pH 7.0) with 50 mM NaCl, 0.1% Tween to a final concentration of 1 uM. The γPNA reporter probes sequence is selected from one or more sequences from Table 24. The well is heated using the afore mentioned protocol and then washed to remove all unbound γPNA reporter probes.

Streptavidin conjugated HRP (VectorLabs, Inc., USA) is added to a final concentration of 1 ng/ml to each microplate well and incubated at room-temperature for 30 min. Post-incubation, each well is washed to remove unbound Streptavidin conjugated HRP. Next, a substrate for HRP, such as SuperSignalFemto (Thermo-Scientific, USA), is added to each well and the emitted optical signal is read on a luminescence plate reader (GloMax 96, Promega, Inc., USA). The presence of *Staphylococcus aureus* in the clinical sample is indicated by an emitted optical signal.

Example 3

Determining if an Infection Arises from Coagulase Negative Staphylococci (CoNS) or from *Staphylococcus aureus*

In one embodiment, γPNA probes are used to identify if a clinical sample is infected with a CoNS species or *Staphylococcus aureus*. The clinical sample originates from an individual who is deemed to have a possible blood-borne infection. *Staphylococcus aureus* or a CoNS species are detected in the sample by adding the sample to wells on a 96-well microplate, wherein some wells are coated with γPNA capture probes specific to *Staphylococcus aureus* and other wells are coated with γPNA capture probes specific to CoNS species. A detectable signal in *Staphylococcus aureus* and/or CoNS species coated wells is indicative of the presence of that bacteria or bacterial family.

In an alternative embodiment, positive and negative control samples are also tested along with the clinical sample. The positive and negative control samples are also added to wells coated with γPNA capture probes specific to *Staphylococcus aureus* or γPNA capture probes specific to CoNS species. The positive controls are samples known to have *Staphylococcus aureus* and/or CoNS species. The negative control sample is known not to have neither *Staphylococcus aureus* and CoNS species.

Methods and Materials

As previously described in Example 2, a 96-well microplate pre-coated with Streptavidin is used as a solid support substrate. Two different γPNA capture probes or sets of capture probes (PNA Innovations, Inc., USA) are added to one or more separate wells. The first well or set of wells contain γPNA capture probes having one or more sequences selected from Table 1, identified as CoNS–. The second well or set of wells, identified as CoNS+, has γPNA capture probes with sequences selected from one of the pools listed in Table 18. The sequences within the pool are pre-mixed at equal-molar concentrations. The sequences found in each pool in Table 18 are unique to a number of CoNS species, which include, but is not limited to, *Staphylococcus capitis, Staphylococcus cohnii, Staphylococcus epidermidis, Staphylococcus haemolyticus, Staphylococcus hominis, Staphylococcus lugdunensis, Staphylococcus saprophyticus, Staphylococcus warneri, Staphylococcus capitis*. The γPNA capture probes are incubated on support substrate for 30 minutes to ensure proper binding. After binding of γPNA capture probes to the wells is completed, the wells are blocked with a biotin wash to saturate remaining biotin binding sites. Post-blocking, the wells are rinsed with a 0.2 micron filtered 10 mM NaPi buffer (pH 7.0).

DNA Amplification

DNA from a clinical patient sample is isolated using a Wizard Genomic Extraction Kit (Promega, Inc., USA). After DNA isolation, the DNA sample is concentrated and amplified using Broad-Range PCR (specific to the 16s region of bacteria) using Phusion DNA polymerase (New England Biolabs, Inc., USA).

The following primers are used for DNA amplification: Forward Primer Sequence: 5' AGA GTT TGA TCC TGG CTC AG (SEQ ID NO: 310); Reverse Primer Sequence: 5' ATC GGC TAC CTT GTT ACG ACT TC (SEQ ID NO: 311).

Both primers are mixed in equal-molar concentrations to a final concentration of 0.5 uM. dNTPs are added, likewise in equal-molar concentrations, to a final concentration of 200 uM each. Phusion is added to a final concentration of 2 u/100 ul with the recommend buffer and DNase/RNase-free water.

Thermocycling conditions are as follows:
1) 45 seconds at 98° C.×1 cycle
2) (15 seconds at 98° C., 30 seconds at 55° C., 75 seconds at 72° C.)×35 cycles
3) 5 minutes at 72° C.×1 cycle Post-PCR processing, the amplified 16s region of the bacterial pathogen is isolated using the DNA Clean-uo kit (DNA Clean and Concentrator—5, Zymo Research, Inc., USA). After completing the DNA clean-up process, biotinylated γPNA reporter probes (PNA Innovations, Inc., USA) with one or more sequence from Table 24 are added to the sample at a final concentration of 1.5 uM in 10 mM NaPi (pH 7.0) and heated for 30 min at 60° C. The biotinylated γPNA reporter probes will invade the bacterial 16s regions. Human DNA cannot be invade as it contains no 16s region.

γPNA Capture Probe Invasion Protocol

The sample is divided and added to both the CoNS– and the CoNS+ wells and incubated with 10 mM NaPi (pH 7.0) with 5 mM NaCl, 0.05% Tween-20 and heated for 30 min to 60° C. Upon completion of the incubation process, both wells are thoroughly rinsed to remove any unbound/uncaptured DNA from each well.

Streptavidin Conjugated HRP Protocol

Streptavidin conjugated HRP (VectorLabs, Inc., USA) is added to a final concentration of 0.75 ng/ml to each well and incubated at room-temperature for 30 min. The Streptavidin conjugated HRP binds to the open biotin site displayed on the γPNA reporter probe. Post incubation, the wells are washed to remove unbound Streptavidin conjugated HRP from the well. Finally, a suitable substrate for HRP, such as SuperSignalFemto (Thermo-Scientific, USA) is added to each well and the emitted optical signal is read on a luminescence plate reader (GloMax 96, Promega, Inc., USA).

Results

If the clinical sample originally contained one or more CoNS species, the CoNS+ well produces a readily detectable optical signal. If the clinical sample originally contained *Staphylococcus aureus*, the CoNS– well produces a readily detectable optical signal. In the case where neither one or more CoNS pathogens or *Staphylococcus aureus* is present in the clinical sample, then both wells remain dark. Likewise, if one or more CoNS species are present in addition to *Staphylococcus aureus*, both the CoNS– and CoNS+ wells emit an optical signal, which is readily detectable. In an alternative embodiment, when an optical signal is produced from the sample, the signal is compared to the positive and negative control samples to determine whether the signal indicates the presence of *Staphylococcus aureus* and/or CoNS species.

Example 4

Discrimination of an Infection Arising from Two Enterococcal Species: *Enterococcus faecalis* and *Enterococcus faecium*

This example demonstrates the ability of γPNA probes to differentiate between two species of bacteria that belong to the same genus. A first sample, which serves as a negative control, is produced by a healthy subject, i.e. does not contain pathogens. The second sample is from an subject suspected of having a possible blood-borne infection. In an alternative embodiment, positive control samples are also tested. The positive controls are a sample or samples known to have *Enterococcus faecalis* and/or *Enterococcus faecium*.

Methods and Materials

Similar to the protocol of Example 2, a 96-well microplate is pre-coated with Streptavidin. In this example, two sets of two or more individual wells are coated with different γPNA capture probe, which have been synthesized to contain a biotin moiety on its N-terminus. In the first set of wells, γPNA capture probes with one or more sequences from Table 2 are introduced into the wells, identified as E_faecalis. In the second sets of wells, γPNA capture probes with one or more sequences from Table 3 are introduced into the well, identified as E_faecium. Binding protocol, posting binding blocking, and wash steps from Example 3 will be applied.

The two samples will be subject to the DNA amplification process and post-PCR processing of Example 3.

Each sample is added to at least one well in each set. All wells will be subjected to the γPNA capture probes invasion protocol and excess DNA wash protocol described in Example 3.

After completing the excess DNA wash protocol, biotinylated γPNA reporter probes with one or more sequence from Table 24 are added to each well at a final concentration of 1.5 uM in 10 mM NaPi (pH 7.0) and heated for 30 min at 60° C. After incubation the wells are washed to remove excess γPNA reporter probes.

Next the wells are subjected to the Streptavidin conjugated HRP protocol detailed in Example 3.

The negative control wells for both *E_faecalis* and *E_faecium* should not yield an optical signal, beyond that which is expected for a sample which contains only non-target genomic material. If however, the clinical sample originally contained pathogens from the bacterial species *Enterococcus faecalis*, the *E_faecalis* wells produce a clearly identifiable optical signal, whereas the *E_faecium* wells do not produce a clearly identifiable optical signal. The reverse would be true if the patient sample originally contained pathogens from the bacterial species *Enterococcus faecium*. Additionally, if the patient is infected by a bacterial of a different species than *Enterococcus faecalis* or *Enterococcus faecium*, or by another pathogen, such as fungal or viral, both well types do not produce a positive readout signature.

Example 5

Discrimination of an Infection Arising from *Candida* Species or *Aspergillus* Species Fungal Pathogens Using Magnetic Beads This example a clinical sample is tested for two different species of bacteria using γPNA capture probes immobilized on a magnetic bead. A negative control, as described in Example 4, is included to determine the presence of the bacterial species in the clinical sample. The clinical sample is from an individual who is deemed to have a possible blood-borne infection that may be caused by *Candida* or *Aspergillus*. In an alternative embodiment, positive control samples are also tested. The positive controls are a sample or samples known to have *Candida* and/or *Aspergillus*.

Methods and Materials

In this embodiment, magnetic beads that have been pre-activated with amine active sites (DynaBeads, M-270 Amine, Inivtrogen, USA) are initialized for the capture of either *Candida* or *Aspergillus*. To produce *Candida* specific magnetic beads, γPNA capture probes incorporating equal-molar concentrations of probes specific to target one or more sequences in Tables 19-22 are covalently bound to the magnetic beads utilizing the manufacturer's standard protocol. Likewise, magnetic beads specific to *Aspergillus* are produced by covalently binding the γPNA capture probes specific to one or more target sequences in Table 23 according to the manufacturer's standard protocol. In both cases, this captures the γPNA capture probes to the surface through their C-terminus. Each functionalized bead set is then placed into a separate microcentrigue tubes; one for the control sample, one for *Candida* species, and one for *Aspergillus* species The two samples are subjected to the DNA amplification process and post-PCR processing discussed in Example 3. The following primers are used for DNA amplification:

```
Forward Primer Sequence:
                                    (SEQ ID NO: 312)
   5' AAA TCA GTT ATC GTT TAT TTG ATA GT;

Reverse Primer Sequence:
                                    (SEQ ID NO: 312)
   5' ATT CCT CGT TGA AGA GCA A.
```

The amplified genomic samples are added to their respective microcentrifuge tubes and incubated for 10 min at 80° C. for 10 min in 10 mM NaPi (pH 7.0) with 15 mM NaCl, 0.1% Tween-20. Upon completion of the incubation process, the magnetic beads are captured into a well or set of wells by a rare earth magnet. The well or sets of wells are rinsed to remove any unbound/uncaptured DNA from each magnetic bead. Post capturing targeted 18s regions, biotinylated γPNA reporter probes with one or more sequence from Table 25 are added to the magnetic beads at a final concentration of 2 μM in 10 mM NaPi (pH 7.0) with 5 mM NaCl, 0.1% Tween-20 and heated at 75° C. for 15 min. After this incubation process, as before, the sample is rinsed/washed through magnetic bead immobilization.

The magnetic beads are then subjected to the Streptavidin conjugated HRP protocol detailed in Example 3.

Results

The optical density from negative control magnetic beads will be negligible and acts a baseline for comparison with the clinical sample. If the clinical sample contained pathogens from *Candida*, the magnetic beads that were functionalized with γPNA specific to *Candida* would yield in increased absorbance compared to the control. If the clinical sample contained pathogens from *Aspergillus*, the magnetic beads that were functionalized with γPNA specific to *Aspergillus* would yield in increased absorbance. If the clinical sample was negative for both *Candida* and *Aspergillus*, then both magnetic bead sets would have an optical density measurement similar to the negative control.

Example 6

Identification of *Escherichia coli* from a Clinical Sample

A solid-support substrate contains the ability to specifically bind and capture a pathogenic genomic target of interest. To achieve this, common glass slides, which have been carboxylated (Xantec Bioanalytics, Germany), are utilized. The glass slides are pre-activated by spotting γPNA capture probes with one or more sequences from Table 4, which is specific to *E. coli*. Binding of the γPNA capture probes to the glass slide is achieved through the N-terminus of the probe and accomplished according to the manufacturer's protocol utilizing 750 nM γPNA capture probe. Post binding, the glass slides are rinsed with a 0.2 micron filtered 10 mM NaPi buffer (pH 7.0).

DNA from a clinical patient sample and a healthy patient (serving as a negative control) are isolated and amplified according to the method described in Example 3. The amplified DNA sample is added to the γPNA capture probe spots on the glass slide. The DNA invasion process is performed under the following conditions; 10 mM NaPi (pH 7.0) with 5 mM NaCl, 0.1% Tween-20, heated to 80° C. for 10 min. Post DNA invasion, the sample is washed. After the wash process, a DNA intercalating dye, Quant-iT PicoGreen (Life Technologies, USA) is added to the spotted samples on the glass slide and incubated at room temperature in a dark room for 20 min. Post incubation, the slide is washed thoroughly to remove non-intercalated dye.

After washing, the glass slide is imaged using an iXon EM-CCD camera (Andor Technology, UK) coupled with a 525 nm long-pass filter (Edmund Optics, USA), where the slide is excited via a 488 nm CW source (Coherent, USA). An optical signal attained from the spot where the γPNA capture probe was initially immobilized would indicate the presence of *E. coli* in the clinical sample.

Example 7

Identification and Quantification of *Staphylococcus epidermis* from a Clinical Sample In some embodiments, γPNA probes are used to identify a pathogen and determine the relative concentration of the pathogen in the clinical sample.

Similar to that which was previously described, a 96-well microplate which pre-coated with Streptavidin. A single individual well or a set of wells contain γPNA capture probes, which have been synthesized to contain a biotin moiety on its N-terminus sequence. The γPNA capture probes have one or more sequences selected from Table 5, which specifically target *Staphylococcus epidermis*. The γPNA capture probe binding protocol of Example 3 is applied.

Known concentrations of *Staphylococcus epidermis* (attained via ATCCA) is added to a pathogen-free sample. A calibration curve is created by using eight different known concentration samples, ranging from $10^0$ to $10^7$ CFU/ml. After adding *Staphylococcus epidermis* to the sample, genomic DNA is extracted using a Wizard Genomic Extraction Kit (Promega, Inc., USA).

The eight samples will be subject to the DNA amplification process and post-PCR processing of Example 3.

After completing the DNA clean-up process, biotinylated γPNA reporter probes with at least three different sequences from Table 24 are added into the sample at a final concentration of 2 uM (per each sequence) in 10 mM Tris-HCl (pH 7.4) 0.05% and heated for 15 min to 75° C. Multiple γPNA reporter probes serve to amplify the number of active sites introduced into the 16s region. This incubation process is done for each of the eight known concentration samples, individually, in γPNA capture probe pre-activated wells. Upon completion of the incubation process, all wells are rinsed to remove any unbound/uncaptured DNA or PNA from each well.

Next, Streptavidin conjugated HRP (VectorLabs, Inc., USA) is added to a final concentration of 1.5 ng/ml to each of the microplate wells and incubated at room-temperature for 15 min. The Streptavidin conjugated HRP binds to the open biotin site displayed on the γPNA reporter probes. Post incubation, the wells are washed to remove unbound Streptavidin conjugated HRP from the well. Finally, a suitable substrate for HRP, such as SuperSignalFemto (Thermo-Scientific, USA) is added to each well and the emitted optical signal is read on a luminescence plate reader (Glo-Max 96, Promega, Inc., USA). The intensity signal is then plotted verse the known concentration which the clean sample was spiked with. This also serves to identify the saturation point of the system and likewise the limit of detection of the system. Negative controls of just the clean sample, which followed the same protocol as the eight known samples, are used to estimate the background signal.

DNA from the clinical patient sample is extracted and isolated using a Wizard Genomic Extraction Kit (Promega, Inc., USA).

DNA is concentrated and the 16s bacterial region is amplified using Broad-Range PCR (specific to the 16s region of bacteria) with the following protocol with Phusion DNA polymerase (New England Biolabs, Inc., USA):

The sample is subjected to the DNA amplification process and post-PCR processing of Example 3.

After completing the DNA clean-up process, an optical signal from the clinical sample is generated using the same protocol used on the eight known samples, discussed above.

The attained optical signal can then be compared to the previously produced calibration curve, thereby enabling an estimation of the pathogen load of *Staphylococcus epidermis*.

Example 8

Gel Shift Assay Demonstrating Binding of *Staphylococcus aureus* γPNA Probes to Target Genomic Material The specificity of γPNA probes designed to target *Staphylococcus aureus* was demonstrated by mixing *Staphylococcus aureus* targeted γPNA probes with either a known sample having *Staphylococcus aureus* genomic material or a known sample negative for *Staphylococcus aureus* genomic material (non-target genomic material). Binding of the γPNA probes to *Staphylococcus aureus* genomic material and lack of binding to non-target genomic material was measured by gel shift assays.

Methods and Materials

γPNA capture probes having sequences that target SEQ ID NO: 7, which targets *Staphylococcus aureus*, were incubated with either a sample of *Staphylococcus aureus* genomic material or a sample having non-target genomic material.

γPNA reporters probes having sequences that target SEQ ID NO: 232, which targets a conserved sequence region common among all bacteria, were incubated with either a sample of *Staphylococcus aureus* genomic material or a sample having non-target genomic material.

A control sample of *Staphylococcus aureus* genomic material without incubation with γPNA probes was included in the assay. See FIG. 2.

The *Staphylococcus aureus* genomic material was ~350 bp DNA fragments that were amplified from *Staphylococcus aureus* (ATCC #43300).

After incubation, the samples were run on a 8% non-denaturing PAGE. The gel was stained for DNA using SybrSafe genomic material intercalating stain.

Results

Figure 2:
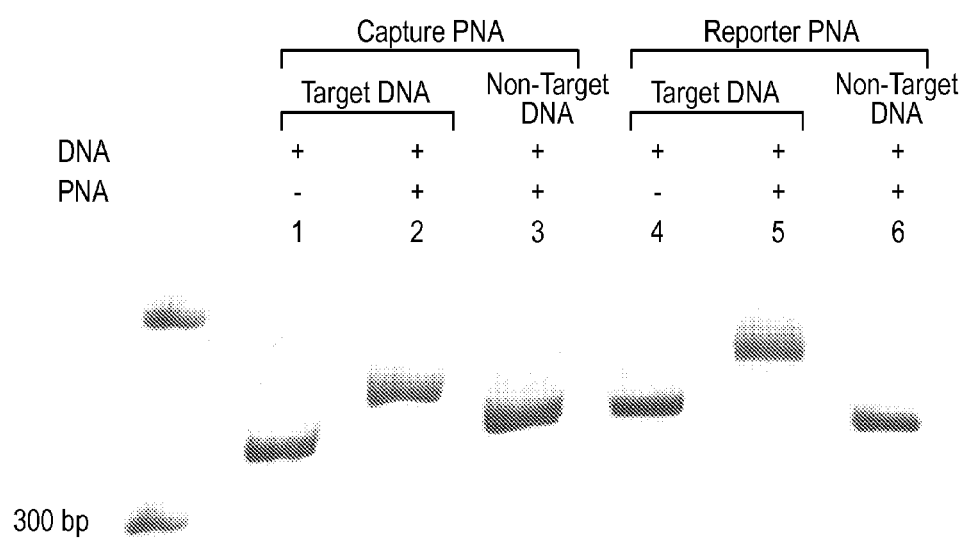
FIG. 2 is a gel shift assay demonstrating the specificity of γPNA probes.

As shown in FIG. 2, γPNA capture probes having sequences targeting SEQ ID NO: 7 were bound to *Staphylococcus aureus* genomic material after incubation (Lane 2), as indicated by the band shift of Lane 2 when compared to Lane 4, which was *Staphylococcus aureus* genomic material without incubation with γPNA probes. Furthermore, Lane 3, which was γPNA capture probes incubated with non-target genomic material, did not show a shift when compared to Lane 4. The shift in Lane 2 and lack of shift in Lane 3, indicates that the γPNA capture probes were bound specifically to the *Staphylococcus aureus* genomic material.

Similar results were seen with the γPNA reporters probes having sequences targeting SEQ ID NO: 232. The γPNA reporters probes also bound specifically to *Staphylococcus* aureus genomic material (FIG. 2, Lane 5). Lane 5, which contained γPNA reporters probes incubated with *Staphylococcus aureus* genomic material, shifts when compared to Lane 4. Additionally, γPNA reporters probes incubated with non-target genomic material, Lane 6, does not shift, as compared to Lane 4. Thus, γPNA reporters probes bound specifically to *Staphylococcus aureus* genomic material.

Example 9

Figure 3:
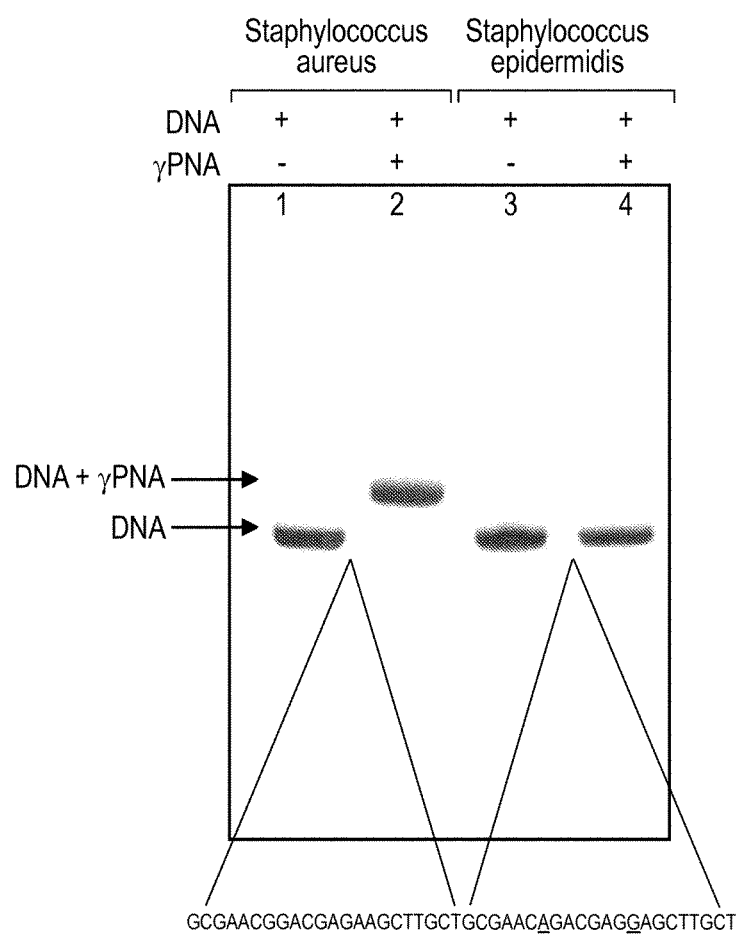
FIG. 3 is a gel shift assay demonstrating the specificity of γPNA capture probes for different species of the same genus.

Gel Shift Assay Demonstrating the Sequence Specificity of *Staphylococcus aureus* γPNA Capture Probes The specificity of γPNA capture probes was demonstrated by comparing the binding of γPNA capture probes targeting *Staphylococcus aureus* to a sample known to have *Staphylococcus aureus* genomic material or to a sample known to have *Staphylococcus epidermis* genomic material.
Materials and Methods γPNA capture probes with sequences targeted at SEQ ID NO: 7, which targets *Staphylococcus aureus*, was combined with a sample that was know to have *Staphylococcus aureus* genomic material. The *Staphylococcus aureus* genomic material was obtained by PCR amplification of the 16s region of *Staphylococcus aureus* DNA. *Staphylococcus aureus* genomic material not incubated with γPNA capture probes was used as a control.

γPNA capture probes with sequences targeted at SEQ ID NO: 7 was also combined with a sample that was know to have *Staphylococcus epidermis* genomic material. The *Staphylococcus epidermis* s genomic material was obtained by PCR amplification of a portion of the 16s region of *Staphylococcus epidermis* DNA. This portion of the 16s region of *Staphylococcus epidermis* differs from the 16s region of *Staphylococcus aureus* by a 2 bp mismatch (indicated by underline in FIG. 3). *Staphylococcus epidermis* genomic material not incubated with γPNA capture probes was used as a control.
Results Referring to FIG. 3, only Lane 2, which contains γPNA capture probes incubated with *Staphylococcus aureus* genomic material, showed a shift when compared to Lane 1 and 3, both contain *Staphylococcus aureus* genomic material not incubated with γPNA capture probes. The shift indicates that the γPNA capture probes were bound to the *Staphylococcus aureus* genomic material. Conversely, the γPNA capture probes incubated with *Staphylococcus epidermis* genomic material, Lane 4, did not show a shift when compared to Lanes 1 and 3. The lack of a shift in Lane 4 indicates that the γPNA capture probes specifically targets *Staphylococcus aureus*.

The specificity of the γPNA capture probes was demonstrated as a 2 bp mismatch prevented the *Staphylococcus aureus* target γPNA capture probes from binding to the *Staphylococcus epidermis* 16s region.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims. The contents of all references cited herein are incorporated by reference in their entireties.

What is claimed is:

1. A method for diagnosing sepsis comprising:
   (a) contacting a plurality of γPNA capture probes to genomic material in a clinical sample obtained from a subject suspected of having sepsis, wherein the γPNA capture probes comprise at least one sequence from one or more of the groups of probes selected from the group consisting of: SEQ ID NOS: 1-18, SEQ ID NOS: 19-22, SEQ ID NOS: 23-28, SEQ ID NOS: 29-34, SEQ ID NOS: 35-38, SEQ ID NOS: 39-57, SEQ ID NOS: 58-72, SEQ ID NOS: 73-91, SEQ ID NOS: 92-94, SEQ ID NOS: 95-97, SEQ ID NOS: 98-110, SEQ ID NOS: 111-113, SEQ ID NOS: 114-117, SEQ ID NOS: 118-119, SEQ ID NOS: 120-121, SEQ ID NOS: 122-153, SEQ ID NOS: 154-166, SEQ ID NOS: 167-190, SEQ ID NOS: 191-193, SEQ ID NOS: 194-196, SEQ ID NOS: 197-211, SEQ ID NOS: 212-215, SEQ ID NOS: 216-230, complementary sequence thereof, and functional equivalents thereof;
   (b) heating the γPNA capture probes and the clinical sample;
   (c) invading a plurality of targeted sepsis-related genomic material by the γPNA capture probes; and
   (d) detecting a presence of one or more targeted genomic material,
   wherein detection of the presence of targeted genomic material is indicative of a sepsis infection.

2. The method of claim 1, wherein the detecting step (d) comprises:
   (i) adding a plurality of γPNA reporter probes comprising at least one sequence from one or both of the groups of probes: SEQ ID NOS: 231-248 and SEQ ID NOS: 249-309, complementary sequence thereof, and functional equivalents thereof;
   (ii) heating the γPNA capture probes, γPNA reporter probes, and the clinical sample and
   (ii) invading of the γPNA reporter probes to the targeted genomic material,
   wherein the γPNA reporter probes are used to detect the targeted genomic material.

3. The method of claim 1, wherein the contacting step (a) is preceded by an amplification step comprising an enzymatic amplification of the targeted sepsis-related genomic material.

4. The method of claim 1, further comprising shearing the genomic material in the sample.

5. The method of claim 1, wherein the γPNA capture probes are bound to a support substrate.

6. The method of claim 5, wherein a first carbon-linker binds the γPNA capture probes to the support substrate, and wherein the first carbon-linker comprises of at least three carbons.

7. The method of claim 5, wherein the support substrate is selected from the group consisting of: a magnetic bead, a well, a plate, a test tube, a stick, a plastic slide, a glass slide, and a biochip.

8. The method of claim 5, wherein the support substrate is coated with Avidin, Neutravidin, or Streptavidin.

9. The method of claim 1, wherein the γPNA capture probes comprise one or more functional moiety selected from the group consisting of: a binding molecule, a spacer group, a linker group, a hydrophobicity-changing group, a charge-inducing group, and a structural change-inducing group.

10. The method of claim 2, wherein the γPNA reporter probes comprise one or more functional moiety selected from the group consisting of: a binding molecule, a spacer group, a linker group, a hydrophobicity-changing group, a charge-inducing group, and a structural change-inducing group.

11. The method of anyone of claim 9 or 10, wherein the spacer group is selected from the group consisting of:

(ethylene)glycol, di(ethylene)glycol, tri(ethylene)glycol, poly(ethylene)glycol, 6-carbon linker, and 12 carbon linker.

12. The method of anyone of claim 9 or 10, wherein the linker group is selected from the group consisting of: COOH group, NHS-ester group, malemide chemistry, Click chemistry, streptavidin, and biotinylation.

13. The method of anyone of claim 9 or 10, wherein the hydrophobicity-changing group is selected from the group consisting of: a naturally polar or charged side group or linker that decreases hydrophobicity, and a naturally apolar and uncharged side group or linker that increases hydrophobicity.

14. The method of anyone of claim 9 or 10, wherein the charge-inducing group is selected from the group consisting of: COOH group, $NH_3$ groups, OH groups, and metallic ions.

15. The method of anyone of claim 9 or 10, wherein the structural change-inducing group induces a chemical modification along the peptide backbone of PNA and is selected from the group consisting of: amino acid-based side chain, nanoparticle, small molecule or intercalating agent.

16. The method of anyone of claim 9 or 10, wherein the γPNA probe comprises biotin or hapten.

17. The method of claim 1, wherein detecting the presence of one or more targeted genomic material is through a signal selected from the group consisting of: fluorescence, luminescence, FRET, colorimetric, calorimetric, interference patterns, pH, resistance/conductivity, enzymatic function and kinetics, protein structure, and electrical potential.

18. The method of claim 2, wherein the γPNA reporter probes comprise a second carbon-linker.

19. The method of claim 18, wherein the second carbon-linker comprises of one or more biotinylation sites.

20. A composition for diagnosing sepsis comprising:
a γPNA probe composition comprising at least one sequence from one or more of the groups of probes selected from the group consisting of: SEQ ID NOS: 1-18, SEQ ID NOS: 19-22, SEQ ID NOS: 23-28, SEQ ID NOS: 29-34, SEQ ID NOS: 35-38, SEQ ID NOS: 39-57, SEQ ID NOS: 58-72, SEQ ID NOS: 73-91, SEQ ID NOS: 92-94, SEQ ID NOS: 95-97, SEQ ID NOS: 98-110, SEQ ID NOS: 111-113, SEQ ID NOS: 114-117, SEQ ID NOS: 118-119, SEQ ID NOS: 120-121, SEQ ID NOS: 122-153, SEQ ID NOS: 154-166, SEQ ID NOS: 167-190, SEQ ID NOS: 191-193, SEQ ID NOS: 194-196, SEQ ID NOS: 197-211, SEQ ID NOS: 212-215, SEQ ID NOS: 216-230, SEQ ID NOS: 231-248, SEQ ID NOS: 249-309, complementary sequence thereof, and functional equivalents thereof.

21. The composition of claim 20, further comprising a support substrate.

22. The composition of claim 21, wherein the support substrate is selected from the group consisting of: a magnetic bead, a well, a plate, a test tube, a stick, a plastic slide, a glass slide, and a biochip.

23. The composition of claim 22, wherein the support substrate is coated with Avidin Neutravidin, or Streptavidin.

24. The composition of claim 20, wherein the γPNA probe comprise one or more functional moiety selected from the group consisting of: a binding molecule, a spacer group, a linker group, a hydrophobicity-changing group, a charge-inducing group, and a structural change-inducing group.

25. The composition of claim 20, wherein the γPNA probe emits a detectable signal selected from the group consisting of: fluorescence, luminescence, FRET, colorimetric, calorimetric, interference patterns, pH, resistance/conductivity, enzymatic function and kinetics, protein structure, and electrical potential.

26. The composition of claim 20, wherein the γPNA probe comprises a carbon linker comprising at least three carbons.

27. The composition of claim 26, wherein the carbon-linker comprises of one or more biotinylation sites.

28. A kit for detecting sepsis comprising:
a γPNA capture probe composition comprising at least one sequence from one or more of the groups of probes selected from the group consisting of: SEQ ID NOS: 1-18, SEQ ID NOS: 19-22, SEQ ID NOS: 23-28, SEQ ID NOS: 29-34, SEQ ID NOS: 35-38, SEQ ID NOS: 39-57, SEQ ID NOS: 58-72, SEQ ID NOS: 73-91, SEQ ID NOS: 92-94, SEQ ID NOS: 95-97, SEQ ID NOS: 98-110, SEQ ID NOS: 111-113, SEQ ID NOS: 114-117, SEQ ID NOS: 118-119, SEQ ID NOS: 120-121, SEQ ID NOS: 122-153, SEQ ID NOS: 154-166, SEQ ID NOS: 167-190, SEQ ID NOS: 191-193, SEQ ID NOS: 194-196, SEQ ID NOS: 197-211, SEQ ID NOS: 212-215, SEQ ID NOS: 216-230, complementary sequence thereof, and functional equivalents thereof.

29. The kit of claim 28, further comprising:
a γPNA reporter probe composition comprising at least one sequence from one or both of the groups of reporter probes: SEQ ID NOS: 231-248 and SEQ ID NOS: 249-309, complementary sequence thereof, and functional equivalents thereof.

30. The kit of claim 28, wherein the γPNA capture probes are bound to a support substrate.

31. The kit of claim 30, wherein the support substrate is selected from the group consisting of: a magnetic bead, a well, a plate, a test tube, a stick, a plastic slide, a glass slide, and a biochip.

32. The kit of claim 31, wherein the support substrate is coated with Avidin, Neutravidin, or Streptavidin.

33. The kit of claim 29, wherein the γPNA probe composition emits a detectable signal selected from the group consisting of: fluorescence, luminescence, FRET, colorimetric, calorimetric, interference patterns, pH, resistance/conductivity, enzymatic function and kinetics, protein structure, and electrical potential.

34. A method for diagnosing sepsis comprising:
(a) contacting a plurality of γPNA reporter probes to genomic material in a clinical sample obtained from a subject suspected of having sepsis, wherein the γPNA reporter probes comprise at least one sequence from one or both of the groups of reporter probes: SEQ ID NOS: 231-248 and SEQ ID NOS: 249-309, complementary sequence thereof, and functional equivalents thereof;
(b) heating the γPNA reporter probes and the clinical sample;
(c) invading a plurality of targeted sepsis-related genomic material by the γPNA reporter probes;
(d) contacting a plurality of γPNA capture probes with sepsis-related genomic material, wherein the γPNA capture probes comprise at least one sequence from one or more of the groups of probes selected from the group consisting of: SEQ ID NOS: 1-18, SEQ ID NOS: 19-22, SEQ ID NOS: 23-28, SEQ ID NOS: 29-34, SEQ ID NOS: 35-38, SEQ ID NOS: 39-57, SEQ ID NOS: 58-72, SEQ ID NOS: 73-91, SEQ ID NOS: 92-94, SEQ ID NOS: 95-97, SEQ ID NOS: 98-110, SEQ ID NOS: 111-113, SEQ ID NOS: 114-117, SEQ ID NOS: 118-119, SEQ ID NOS: 120-121, SEQ ID NOS: 122-153, SEQ ID NOS: 154-166, SEQ ID NOS: 167-190, SEQ ID NOS: 191-193, SEQ ID NOS: 194-196, SEQ ID NOS: 197-211, SEQ ID NOS: 212-215, SEQ ID NOS: 216-230, complementary sequence thereof, and functional equivalents thereof and wherein the γPNA capture probes are bound to a support substrate;

(e) heating the γPNA reporter probes, the γPNA capture probes, and the clinical sample;

(f) invading the plurality of targeted sepsis-related genomic material by the γPNA capture probes; and (g) detecting a presence of one or more targeted genomic material, wherein detection of the presence of target genomic material is indicative of sepsis infection.

35. The method of claim 34, wherein the support substrate is selected from the group consisting of: a magnetic bead, a well, a plate, a test tube, a stick, a plastic slide, a glass slide, and a biochip.

36. The method of claim 34, wherein the support substrate is coated with Avidin, Neutravidin, or Streptavidin.

37. The method of claim 34, wherein the γPNA capture probes and γPNA reporter probes comprise one or more functional moiety selected from the group consisting of: a binding molecule, a spacer group, a linker group, a hydrophobicity-changing group, a charge-inducing group, and a structural change-inducing group.

38. The method of claim 34, wherein the γPNA capture probes and γPNA reporter probes comprise biotin or hapten.

39. The method of claim 34, wherein the γPNA reporter probes emit a detectable signal selected from the group consisting of: fluorescence, luminescence, FRET, colorimetric, calorimetric, interference patterns, pH, resistance/conductivity, enzymatic function and kinetics, protein structure, and electrical potential.

\* \* \* \* \*